(12) United States Patent
Exner et al.

(10) Patent No.: US 9,320,757 B2
(45) Date of Patent: *Apr. 26, 2016

(54) METHOD FOR TREATING A NEOPLASTIC DISORDER

(75) Inventors: Agata Exner, Westlake, OH (US); Tianyi Krupka, Westlake, OH (US); Brent Weinberg, Cleveland Heights, OH (US); John Haaga, Chagrin Falls, OH (US)

(73) Assignee: Case Western Reserve University, Cleveland, OH (US)

( * ) Notice: Subject to any disclaimer, the term of this patent is extended or adjusted under 35 U.S.C. 154(b) by 1202 days.

This patent is subject to a terminal disclaimer.

(21) Appl. No.: 11/947,375

(22) Filed: Nov. 29, 2007

(65) Prior Publication Data

US 2008/0206187 A1 Aug. 28, 2008

Related U.S. Application Data

(60) Provisional application No. 60/861,618, filed on Nov. 29, 2006.

(51) Int. Cl.
*A61K 31/765* (2006.01)
*A61P 35/00* (2006.01)

(52) U.S. Cl.
CPC .................................... *A61K 31/765* (2013.01)

(58) Field of Classification Search
CPC .................................................... A61K 31/765
See application file for complete search history.

(56) References Cited

U.S. PATENT DOCUMENTS 5,595,756 A * 1/1997 Bally et al. .................... 424/450

OTHER PUBLICATIONS

Paul Calabresi & Bruce Chabner, Chemistry of Neoplastic Disease in Goodman & Gilman's The Pharmacologic Basis of Therapeutics, tenth edition, MCGraw-Hill (2001) p. 1381, 1388.*
G. Scott Gazelle, et al, Tumor Ablation with Radio-frequency Energy, 217 Radiology 633 (2000).*
Giammaria Fiorentini, Hyperthermia Today: Electric Energy, a New Opportunity in Cancer Treatment, 2 J Cancer Res. 41 (Jun. 2002).*
Alexander Kabanov, et al, An Essential Relationship Between ATP Depletion and Chemosensitizing Activity of Pluronic Block Copolymers, 91 J Control. Rel. 75 (2003).*
Elena Batrakova, et al, Sensitization of Cells Overexpressing Multidrug-Resistant Proteins by Pluronic P85, 20 Pharm. Res. 1581 (Oct. 2003).*
Valery Alakhov, et al, Hypersensitization of Multiudrug-Resistant Human Ovarian Carcinoma Cells by Pluronic P85 Block Copolymer, 7 Bioconjug. Chem. 209 (1996).*
S. Nahum Goldberg, et al, Percutaneous Tumor Ablation: Increased Necrosis with Combined Radio-Frequency Ablation and Intravenous Liposome Doxorubicin in an Rat Breast Tumor Model, 222 Radiology 797 (2002).*
Sporn et al, "Chemoprevention of Cancer," Carcinogenesis, vol. 21 (2000), 525-530.*
Auerbach et al. Cancer and Metastasis Reviews, 2000, 19: 167-172.*
Batrakova et al. "Fundamental Relationships Between the Composition of Pluronic Block Copolymers and Their Hypersensitization Effect in MDR Cancer Cells." Pharmaceutical Research, 1999, 16(9): 1373-1379.*
Wells et al. "Localized delivery to CT-26 tumors in mice using thermosensitive liposomes." International Journal of Pharmaceutics, 2003, 162: 105-114.*
Batrakova et al. (British Journal of Cancer (2001) 85(12), 1987-1997).*
Aetna."Hypertermia in Cancer Therapy." Retrieved on Feb. 10, 2015. Retrieved from the internet <URL: http://www.aetna.com/cpb/medical/data/200_299/0278.html>.*

* cited by examiner

*Primary Examiner* — Anoop Singh
*Assistant Examiner* — Doan Phan
(74) *Attorney, Agent, or Firm* — Tarolli, Sundheim, Covell & Tummino LLP

(57) ABSTRACT

A method for treating a neoplastic disorder in a subject includes administering to the neoplastic cells a neoplastic cell-sensitizing composition including a poly(ethylene oxide)-poly(propylene oxide) copolymer. The poly(ethylene oxide)-poly(propylene oxide) copolymer can sensitize the neoplastic cells to hyperthermia. Energy can be applied to the neoplastic cells to heat and ablate the cells.

18 Claims, 13 Drawing Sheets

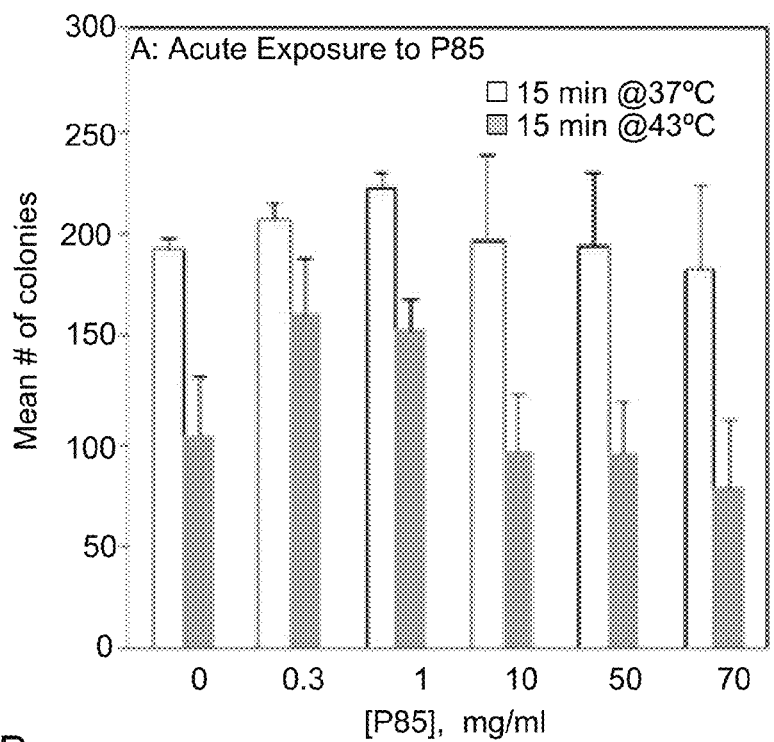
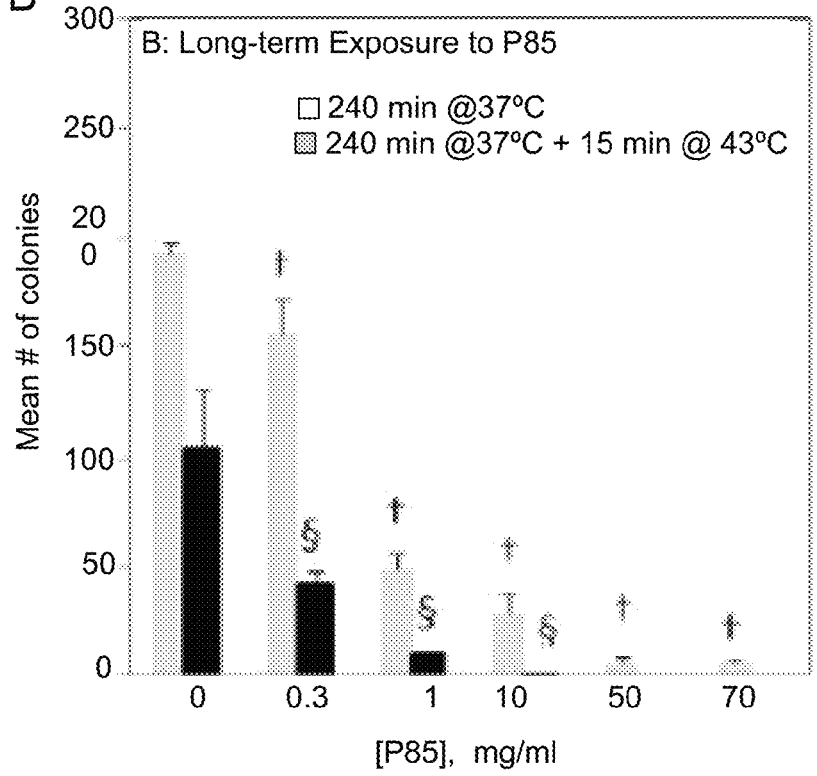
FIGS. 11A-B

METHOD FOR TREATING A NEOPLASTIC DISORDER

RELATED APPLICATION

This application claims priority from U.S. Provisional Application No. 60/861,618, filed Nov. 29, 2006, the subject matter of which is incorporated herein by reference.

GOVERNMENT FUNDING

This invention was made with government support under Grant No. NBIB/NIH R21EB002847 awarded by the National Institutes of Health. The United States government has certain rights in the invention.

TECHNICAL FIELD

The present invention generally relates to methods for treating diseases, and more particularly to methods for treating neoplastic disorders using polymers and thermal ablation therapy.

BACKGROUND OF THE INVENTION

Image-guided interventions have become a viable treatment alternative for selected cancer patients because they provide expeditious, efficacious, and cost-effective management of localized cancer sites. Among the various reported methods, minimally-invasive radiofrequency (RF) ablation has become the standard of care because of its predictability, ease of use, and favorable results.

Since its clinical debut in 1995, RF ablation has become an increasingly powerful tool for treatment of primary metastatic malignancy in a variety of sites (e.g., the liver, pancreas, and kidneys) in patients who are otherwise unsuitable candidates for surgical tumor resection. The success of RF ablation has resulted in increased patient survival and a low rate of major complications. Additionally, recent technological developments such as cooled or multi-tipped electrodes have further increased the scope of tumors that can be treated with RF ablation. Nonetheless, peripheral cooling of tumor tissue near major blood vessels, restricted size of the energy deposition, and seeding of residual tumor around needle electrode tracks have all been associated with local tumor re-growth after RF ablation.

Pharmacological agents have been used as an adjuvant to improve clinical outcomes associated with RF therapy. While efficacious, such pharmacological agents are cytotoxic and non-specific. Consequently, the use of pharmacological agents with RF ablation often leads to inadvertent normal cell death. An ideal agent for co-administration with RF ablation would maximize tumor ablative effects while also limiting damage to normal tissue.

SUMMARY OF THE INVENTION

The present invention generally relates to methods for treating diseases, and more particularly to methods for treating neoplastic disorders using polymers and thermal ablation therapy. According to one aspect of the present invention, a method is provided for treating a neoplastic disorder in a subject. One step of the method can include administering to the neoplastic cells a neoplastic cell-sensitizing composition comprising a poly(ethylene oxide)-poly(propylene oxide) copolymer. The poly(ethylene oxide)-poly(propylene oxide) copolymer can sensitize the neoplastic cells to hyperthermia. Energy can be applied to the sensitized neoplastic cells to heat and ablate the cells.

According to another aspect of the present invention, a method is provided for treating a tumor in a subject. One step of the method can include administering to neoplastic cells of the tumor a neoplastic cell-sensitizing composition comprising a poloxamer. The poloxamer can sensitize the tumor to hyperthermia. Energy can be applied to the sensitized neoplastic cells of the tumor to heat and ablate the sensitized neoplastic cells.

According to another aspect of the present invention, a method is provided for treating a tumor in a subject. One step of the method can include administering to neoplastic cells of the tumor a neoplastic cell-sensitizing composition comprising a poloxamer. The poloxamer can sensitize the tumor to hyperthermia. Radiofrequency energy can be applied to the sensitized neoplastic cells of the tumor to ablate the sensitized neoplastic cells.

BRIEF DESCRIPTION OF THE DRAWINGS

The foregoing and other features of the present invention will become apparent to those skilled in the art to which the present invention relates upon reading the following description with reference to the accompanying drawings, in which:

(FIG. 2A) and 43° C. (FIG. 2B). Each measurement is the mean of 16 wells±SEM, and (*) indicates the treatment is significantly different from control;

FIG. 5A is an overview slide showing treated region abutting a large untreated tumor nodule. The locations of high magnification images are noted with black rectangles. Original image 40×, scale bar 2 mm. FIG. 5B is a detailed image of coagulated region with granulation tissue and inflammatory cells. Original image 250×, scale bar 100 μm. FIG. 5C is a high magnification image of a tumor nodule with highly irregular, poorly differentiated, viable tumor cells. Original image 250×, scale bar 100 μm;

FIG. 6A is an overview slide showing treated region abutting a large untreated tumor nodule. The locations of high magnification images are noted with black rectangles. Original image 40×, scale bar 2 mm. FIG. 6B is a detailed image of coagulated region with granulation tissue and inflammatory cells. Original image 250×, scale bar 100 μm. FIG. 6C is a high magnification image of a tumor nodule with highly irregular, poorly differentiated, viable tumor cells. Original image 250×, scale bar 100 μm;

FIGS. 11A-B are a series of graphs showing the mean number of colonies after acute (15 min) and long-term (240 min) P85 exposure with and without additional heat treatment (n=3, Mean±SEM). FIG. 11A shows no significant difference between treatment groups. In FIG. 11B, § designates statistically significant differences vs. combination of P85 exposure with heat.

DETAILED DESCRIPTION

Figure 1:
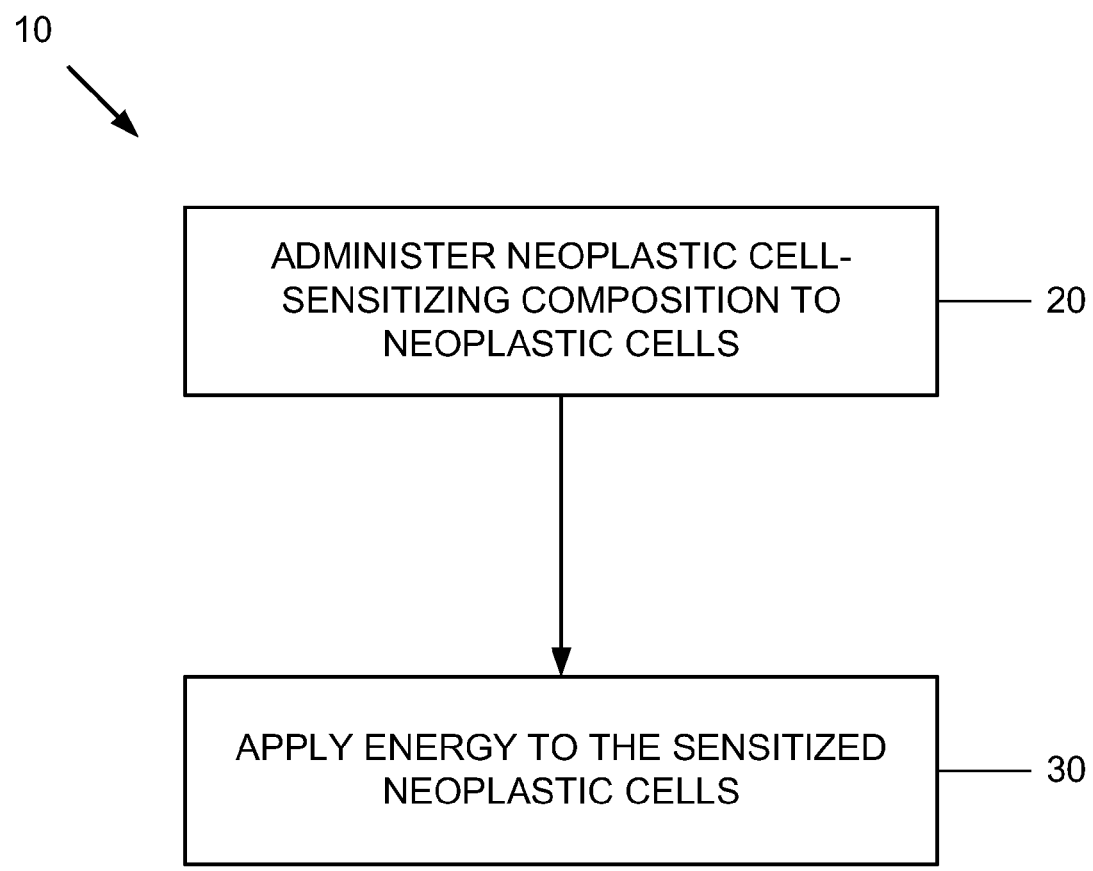
FIG. 1 is a flowchart illustrating a method for treating a tumor according to one aspect of the present invention.

The present invention generally relates to methods for treating diseases, and more particularly to methods for treating neoplastic disorders using polymers and thermal ablation therapy. It was found that a non-toxic, neoplastic cell-sensitizing composition comprising at least one polymer can be used to sensitize neoplastic cells to thermal energy (e.g., radio frequency (RF) ablation therapy). The neoplastic cell-sensitizing composition can include a poly(ethylene oxide)-poly(propylene oxide) copolymer that increases tumor susceptibility to RF ablation while also limiting damage to normal cells. The present invention therefore provides a method for maximizing the effects of thermal ablation therapy while limiting damage to normal tissue.

All scientific and technical terms used in this application have meanings commonly used in the art unless otherwise specified. The definitions provided herein are to facilitate understanding of certain terms used frequently herein and are not meant to limit the scope of the present invention.

In the context of the present invention, the term "neoplastic disorder" refers to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" refers to an abnormal mass or population of cells that result from excessive cell division, whether malignant or benign, and all pre-cancerous and cancerous cells and tissues.

As used herein, the terms "treating" or "treatment" of a neoplastic disease refer to executing a treatment protocol, which may include injecting a neoplastic cell-sensitizing composition into a subject and then applying energy to eradicate at least one neoplastic cell. Thus, "treating" or "treatment" does not require complete eradication of neoplastic cells.

As used herein, the term "polymer" refers to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

As used herein, the term "block copolymer" refers to a polymer in which adjacent polymer segments or blocks are different, i.e., each block comprises a unit derived from a different characteristic species of monomer or has a different composition of units.

As used herein, the term "poloxamer" refers to a series of non-ionic surfactants comprised of block copolymers of ethylene oxide and propylene oxide. Poloxamers are synthesized by the sequential addition of propylene oxide, followed by ethylene oxide, to propylene glycol. The poly(oxyethylene) segment is hydrophillic and the poly(oxypropylene) segment is hydrophobic. The molecular weight of poloxamers may range from 1000 to greater than 16000. The basic structure of a poloxamer is $HO\text{---}(C_2H_4O)_a(C_3H_6O)_b(C_2H_4O)_a\text{---}H$, where "a" and "b" represent repeating units of ethylene oxide and propylene oxide, respectively.

As used herein, the term "poloxamine" refers to a polyalkoxylated symmetrical block copolymer prepared from an ethylene diamine initiator. Poloxamines are synthesized using the same sequential order of addition of alkylene oxides as used to synthesize poloxamers. Structurally, the poloxamines include four alkylene oxide chains and two tertiary nitrogen atoms, at least one of which is capable of forming a quaternary salt. Poloxamines are also terminated by primary hydroxyl groups.

As used herein, the term "meroxapol" refers to a symmetrical block copolymer consisting of a core of PEG polyoxypropylated to both its terminal hydroxyl groups, i.e., conforming to the general type $(PPG)_x\text{-}(PEG)_y\text{-}(PPG)_x$, and being formed by an ethylene glycol initiator. As opposed to the poloxamers, which are terminated by two primary hydroxyl groups, meroxapols have secondary hydroxyl groups at the ends and the hydrophobe is split in two, each half on the outside of the surfactant.

As used herein, the term "neoplastic cell-sensitizing composition" refers to a composition comprising at least one polymer capable of sensitizing a neoplastic cell to thermal energy. By "sensitizing" it is meant that the neoplastic cell exhibits an increased sensitivity or reduced resistance to thermal energy. An increased sensitivity or reduced resistance of a neoplastic cell may be measured according to methods known in the art, e.g., cell proliferative assays and tumor size reduction.

FIG. 1 is a flow diagram illustrating a method 10 in accordance with the present invention for treating a neoplastic disorder (or disease) in a subject. As used herein, the term "subject" refers to any human, non-human primate, cow, horse, pig, sheep, goat, dog, cat or rodent. Generally, neoplastic diseases treatable by the present invention can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells.

According to one aspect of the present invention, a subject having at least one neoplastic cell, such as a tumor, may be identified using methods known in the art. For example, the anatomical position, gross size, and/or cellular composition of the neoplastic cell may be determined using contrast-enhanced MRI or CT. Additional methods for identifying neoplastic cells can include, but are not limited to, ultrasound, bone scan, surgical biopsy, and biological markers (e.g., serum protein levels and gene expression profiles). As described in greater detail below, an imaging solution comprising a neoplastic cell-sensitizing composition of the present invention may be used in combination with MRI or CT, for example, to identify neoplastic cells.

At 20, a neoplastic cell-sensitizing composition may be administered (e.g., injected) to a subject after the neoplastic cells have been identified. As described in more detail below, the neoplastic cell-sensitizing composition can include a block copolymer, such as a poly(ethylene oxide)-poly(propylene oxide) copolymer. The neoplastic cell-sensitizing composition can sensitize the neoplastic cells to hyperthermia. Administration of the neoplastic cell-sensitizing composition to the neoplastic cells can lead to an increase in coagulation necrosis and an improved likelihood of neoplastic cell (e.g., tumor) eradication using thermal ablation therapy.

In general, the neoplastic cell-sensitizing composition may be responsive to, or affected by, thermal energy. For example, the neoplastic cell-sensitizing composition may undergo a phase shift when the temperature of the neoplastic cell-sensitizing composition passes through a lower critical solution temperature (LCST). Above the LCST, the neoplastic cell-sensitizing composition may tend to become dehydrated, in turn making it less soluble in water.

As noted above, the neoplastic cell-sensitizing composition can include a block copolymer, such as a poly(ethylene oxide)-poly(propylene oxide) block copolymer. Examples of poly(ethylene oxide)-poly(propylene oxide) block copolymers are poloxamers, poloxamines, meroxapols, and combinations thereof.

The poloxamer can comprise any one or combination of a series of non-ionic surfactants including block copolymers of ethylene oxide and propylene oxide. The poly(oxyethylene) (PEO) and poly(oxypropylene) (PPO) segments may be hydrophilic and hydrophobic, respectively. The poloxamer may be a liquid, a paste or a solid, and may have a molecular weight that ranges from about 1000 to greater than about 16000.

The basic chemical formula of the poloxamer may be HO—$(C_2H_4O)_a(C_3H_6O)_b(C_2H_4O)_a$—H, where "a" and "b" represent repeating units of PEO and PPO, respectively. More particularly, the at least one poloxamer may have the chemical formula of HO—$(C_2H_4O)_a(C_3H_6O)_b(C_2H_4O)_a$—H, where "a" is about 2 to about 130 and "b" is about 16 to about 70. It should be appreciated that the poloxamer may comprise a reverse poloxamer if the ethylene oxide segment is sandwiched between two propylene oxide segments (i.e., PPO-PEO-PPO).

The poloxamer may be commercially available under various trade names including, for example, LUTROL, PLURONIC, SYNPERONIC (ICI), EMKALYX, PLURACARE, and PLURODAC. Examples of the PLURONIC series are PLURONIC L121 (avg. MW: 4400), PLURONIC L101 (avg. MW: 3800), PLURONIC L81 (avg. MW: 2750), PLURONIC L61 (avg. MW: 2000), PLURONIC L31 (avg. MW: 1100), PLURONIC L122 (avg. MW: 5000), PLURONIC L92 (avg. MW: 3650), PLURONIC L72 (avg. MW: 2750), PLURONIC L62 (avg. MW: 2500), PLURONIC L42 (avg. MW: 1630), PLURONIC L63 (avg. MW: 2650), PLURONIC L43 (avg. MW: 1850), PLURONIC L64 (avg. MW: 2900), PLURONIC L44 (avg. MW: 2200), PLURONIC L35 (avg. MW: 1900), PLURONIC P123 (avg. MW: 5750), PLURONIC P103 (avg. MW: 4950), PLURONIC P104 (avg. MW: 5900), PLURONIC P84 (avg. MW: 4200), PLURONIC P105 (avg. MW: 6500), PLURONIC P85 (avg. MW: 4600), PLURONIC P75 (avg. MW: 4150), PLURONIC P65 (avg. MW: 3400), PLURONIC F127 (avg. MW: 12600), PLURONIC F98 (avg. MW: 13000), PLURONIC F87 (avg. MW: 7700), PLURONIC F77 (avg. MW: 6600), PLURONIC F108 (avg. MW; 14600), PLURONIC F98 (avg. MW: 13000), PLURONIC F88 (avg. MW: 11400), PLURONIC F68 (avg. MW: 8400), and PLURONIC F38 (avg. MW: 4700).

Examples of reverse poloxamers are PLURONIC R 31R1 (avg. MW: 3250), PLURONIC R 25R1 (avg. MW: 2700), PLURONIC R 17R1 (avg. MW: 1900), PLURONIC R 31R2 (avg. MW: 3300), PLURONIC R 25R2 (avg. MW: 3100), PLURONIC R 17R2 (avg. MW: 2150), PLURONIC R 12R3 (avg. MW: 1800), PLURONIC R 17R4 (avg. MW: 4150), PLURONIC R 25R4 (avg. MW: 1600), PLURONIC R 22R4 (avg. MW: 3350), PLURONIC R 17R4 (avg. MW: 3650), PLURONIC R 25R5 (avg. MW: 4320), PLURONIC R 10R5 (avg. MW: 1950), PLURONIC R 25R8 (avg. MW: 8550), PLURONIC R 17R8 (avg. MW: 7000), and PLURONIC R 10R8 (avg. MW: 4550).

Other commercially available poloxamers can include compounds that are block copolymers of polyethylene and polypropylene glycol, such as SYNPERONIC L121, SYNPERONIC L122, SYNPERONIC P104, SYNPERONIC P105, SYNPERONIC P123, SYNPERONIC P85, SYNPERONIC P94, and compounds that are nonylphenyl polyethylene glycol such as SYNPERONIC NP10, SYNPERONIC NP30 and SYNPERONIC NP5.

In another aspect of the present invention, the poloxamer can have the chemical formula HO—$(C_2H_4O)_{26}(C_3H_6O)_{40}(C_2H_4O)_{26}$—H (PLURONIC P85).

The poloxamine can include a polyalkoxylated symmetrical block copolymer prepared from an ethylene diamine initiator. Poloxamines are synthesized using the same sequential order of addition of alkylene oxides as used to synthesize poloxamers. Structurally, the poloxamines can include four alkylene oxide chains and two tertiary nitrogen atoms, at least one of which is capable of forming a quaternary salt. Poloxamines can also be terminated by primary hydroxyl groups. Examples of poloxamines are the TETRONIC and/or TETRONIC R series produced by BASF. For example, poloxamines can include TETRONIC 904, TETRONIC 908, TETRONIC 1107, TETRONIC 90R4, TETRONIC 1304, TETRONIC 1307 and TETRONIC T1501.

Meroxapols can include symmetrical block copolymer consisting of a core of PEG polyoxypropylated to both its terminal hydroxyl groups, i.e., conforming to the general type $(PPG)_x$-$(PEG)_y$-$(PPG)_x$, and being formed by an ethylene glycol initiator. Examples of meroxapols are MEROXAPOL 105, MEROXAPOL 108, MEROXAPOL 172, MEROXAPOL 174, MEROXAPOL 252, MEROXAPOL 254, MEROXAPOL 258 and MEROXAPOL 311.

It will be appreciated that the neoplastic cell-sensitizing composition may further comprise a pharmaceutically acceptable carrier. Pharmaceutically acceptable carriers may include any material or materials which are not biologically or otherwise undesirable, i.e., the material may be incorporated into the neoplastic cell-sensitizing composition without causing any undesirable biological effects or interacting in a deleterious manner with any of the other components of the neoplastic cell-sensitizing composition. When the term pharmaceutically acceptable is used to refer to a pharmaceutical carrier, it is implied that the carrier has met the required standards of toxicological and manufacturing testing or that it is included on the Inactive Ingredient Guide prepared by the U.S. Food and Drug administration.

The location(s) where the neoplastic cell-sensitizing composition is administered to the subject may be determined based on the subject's individual need, such as the location of the neoplastic cells (e.g., the position of a tumor, the size of a tumor, and the location of a tumor on or near a particular organ). For example, the neoplastic cell-sensitizing composition may be injected directly (i.e., intratumorally) into a tumor. Alternatively, the neoplastic cell-sensitizing composition may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

At 30, energy may be applied to the sensitized neoplastic cells before, after, or during injection of the neoplastic cell-sensitizing composition. The energy may comprise electromagnetic energy, ultrasound energy, or a combination thereof, and may be delivered via an RF energy source, an x-ray energy source, an infrared radiation source, a far infrared radiation source, an ultraviolet (UV) radiation source, a long-wavelength UV radiation source, a source of visible light, a laser microwave and/or a γ-ray radiation source. The energy can be delivered directly to the sensitized neoplastic cells via a probe, for example, or via an external energy source to penetrate through the tissue of the subject. Where an external energy source is used, the depth of penetration can be controlled by the wavelength of the energy used. For example, visible light may be used instead of UV radiation as visible light penetrates more deeply through tissue than does UV radiation.

In another aspect of the present invention, a sensitizing solution may be administered to the subject before, during, or after delivery of energy to the tumor site. The sensitizing solution may comprise a sodium chloride solution, such as saline, and may be administered directly into the sensitized neoplastic cells or intravenously. Alternatively, the sensitizing solution may be combined with the neoplastic cell-sensitizing composition and then injected into the subject. Administration of the sensitizing solution may improve energy deposition at the energy site, increase tissue heating, and induce coagulation within the tumor.

The anatomical and physiological effects of energy delivery to the sensitized neoplastic cells may be monitored using techniques known in the art. For example, functional MRI (fMRI), MR spectroscopy (MRS) or functional CT may be used to monitor longitudinal changes in tissue perfusion and/or metabolism within the sensitized neoplastic cells as energy is being applied. Other techniques, such as cell viability and/or proliferation assays, may also be used to monitor the effects of energy delivery to the sensitized neoplastic cells. Depending upon the observed effects of energy delivery to the sensitized neoplastic cells, the method 10 may be repeated as needed. For example, if fMRI indicates that a tumor is partially ablated, then energy may be re-applied to the tumor until the tumor is entirely ablated.

In another aspect of the present invention, at least one chemotherapeutic agent may be administered to the subject in conjunction with or after applying energy to the sensitized neoplastic cells. Examples of chemotherapeutic agents include, but are not limited to, doxorubicin, cisplatin, etoposide, vinblastine, vincristine, estrumustine, suramin, staurosporine, paclitaxel, angiogenstatin, and estastatin. Administering a chemotherapeutic agent helps to ensure that any non-ablated neoplastic cells are destroyed (e.g., complete tumor eradication).

In an example of the method 10, a human subject having a solid tumor, such as a colorectal carcinoma, may be treated in accordance with one aspect of the present invention. As described above, the location, size, and composition of the carcinoma may be identified using contrast-enhanced MRI or CT, for example. Next, a neoplastic cell-sensitizing composition comprising about 1 wt % of PLURONIC P85 may be intravenously injected into the subject. A 1.5T MRI device may then be used to image the carcinoma. Alternatively, where the carcinoma is imaged using a non-PLURONIC-based imaging agent, a neoplastic cell-sensitizing composition comprising about 7 wt % of PLURONIC P85 may be injected directly into the carcinoma.

After injecting the neoplastic cell-sensitizing composition, RF energy may be applied to the carcinoma. For example, monopolar RF energy may be applied using a 480-kHz RF generator (3E, RADIONICS) and a needle electrode. The needle may be surgically inserted into the carcinoma. Next, RF energy may be applied to the needle for a desired period of time and at a desired temperature. For example, RF energy may be applied at about 43° C. to about 100° C. for about 1 minute to about 100 minutes or greater. The carcinoma may be again imaged using CT or fMRI, for example, during and/or after delivery of RF energy to assess any longitudinal changes in carcinoma tissue perfusion and/or metabolism within the carcinoma. The method 10 may then be repeated as needed until the carcinoma is entirely ablated.

Although the exact mechanism is unknown, any one or combination of several mechanisms may account for the present invention. For example, cellular ATP depletion in neoplastic cells may decrease the ability of heat-damaged cells to recover from sublethal hyperthermic injury. Alternatively, altered gene expression, such as a decrease in anti-apoptotic or heath shock gene expression, may increase the number of neoplastic cells undergoing apoptosis. Further, the neoplastic cell-sensitizing composition of the present invention may disrupt neoplastic cell membranes and thus leave the cells more vulnerable to heat damage. It should be appreciated, however, that the potential mechanisms provided above are speculative only, and are not intended to be limiting.

The following examples are for the purpose of illustration only and are not intended to limit the scope of the claims, which are appended hereto.

Example 1

Materials and Methods

All animal experiments were approved by the Institutional Animal Care and Use Committee at Case Western Reserve University and followed all applicable guidelines on animal use.

Pluronic Solutions

P85 solutions were created by dissolving P85 paste (donated to A.A.E. by BASF, Shreveport, La.) in Roswell Park Memorial Institute medium 1640 (RPMI) with L-glutamine (GIBCO, Grand Island, N.Y.) at concentrations of 1, 7, and 10% (w/w). Solutions were filtered with a sterile 0.22 µm syringe filter (Millex TM-GP, Millipore, Billerica, Mass.) and stored at 4° C. RPMI was used as a solvent in all studies to maintain consistency between cell and animal experiments.

In Vitro Cytotoxicity

Cytotoxicity of P85 solutions was determined on a rat colorectal carcinoma cell line (DHD/K12/TRb) in vitro (T.M.K.). This cell line, which originated from a 1,2-dimethylhydrazine-induced colon adenocarcinoma in BDIX/CrCr-1BR (BD-IX) rats, is a model of metastatic colon carcinoma that can be propagated both in vitro and in vivo. Cells from this line were donated by Dr. W. G. Pitt, Brigham Young University (original source, European Collection of Cell Cultures). The cells were grown in RPMI containing 10% fetal bovine serum (FBS, Hyclone, Logan, Utah) and 1% penicillin/streptomycin (GIBCO) and passaged weekly. For cytotoxicity studies, cells were detached with trypsin-EDTA (GIBCO), resuspended in RPMI, and plated into 96-well plates at $10^5$ cells/ml. After 24 hours, the media was replaced with 0, 7 or 10% P85 solution, and the cells were placed in a covered water bath in an incubator at 37° C. or 43±1° C. (C24, New Brunswick Scientific, Edison, N.J.) for 15, 30, or 60 minutes. The cells were washed and incubated overnight before measuring mitochondrial enzyme activity with the QIA127 colorimetric assay (Oncogene, Cambridge, Mass.). Absorbance data was collected with a plate reader (ELx808, Bio-Tek, Winooski, Vt.), and the results were determined by averaging the absorbance of 16 individual wells. Mitochondrial enzyme viability was then compared between cells treated with P85 and controls at each temperature.

Cell proliferation ability was assessed with a clonogenic survival study. Cells were plated into 6-well plates at $10_5$ cells/ml, and after 24 hours cells were again treated with 1 or 7% P85 solution at 37° C. or 43±1° C. for 30 or 60 minutes. The treated cells were washed, diluted to 700 cells/ml, and replated. After 9 days, cells were fixed in methanol and stained with May-Grunwald and Giemsa stains (Sigma-Aldrich, St. Louis, Mo.); stained colonies with greater than 50 cells were then counted manually. Resulting colony forming ability was determined using the mean number of colonies in 3 plates. Results were assessed by comparing cells treated with P85 against control cells at each temperature.

Tumor Inoculation

Tumors for use in in vivo studies were inoculated subcutaneously (B.D.W and T.M.K) in a total of 41 BD-IX rats, with 9 of 41 used for coagulation necrosis measurement [see below]. On the day of inoculation, cells were trypsinized and resuspended in RPMI at a final concentration of $2\times10^6$ cells/ml. BD-IX rats were obtained from an in-house rat colony (original source, Charles River Laboratories, Wilmington, Mass.). The rats were anesthetized with 1% isoflurane and an $O_2$ flow rate of 1 L/m (EZ150 Isoflurane Vaporizer, EZ Anesthesia, Palmer, Pa.). Tumors were inoculated bilaterally on the back, approximately 1 cm distal to the scapula and 1 cm lateral to the midline by subcutaneous injection of 50 µl of the cell suspension.

Tumor Treatment

Four weeks after tumor inoculation, rats were anesthetized, the tumor site was shaved and cleaned, and tumor size was measured with calipers (B.D.W. and T.M.K). Rats were then randomly assigned to three groups. If tumors had not developed by this time or were too small to be treated, they were excluded from further study prior to treatment. In the first group (control), both tumors were treated with RF ablation only (7 rats, 14 tumors). In the second group (local P85), the right tumor was treated with a local injection of 100 µl 7% P85 solution (mean dose 28.1 mg/kg) into the center of the tumor followed by RF ablation 15 minutes later (13 rats, 13 tumors), while the left tumor was treated with RF ablation alone. The time after intratumoral injection was chosen to give the liquid time to be absorbed into the surrounding tumor tissue and minimize leakage during the ablation. Only one tumor was treated to limit confounding effects of systemic exposure to P85 in the contralateral tumor. The third group of rats (systemic P85) was given an intravenous injection of 100 µl 1% P85 (mean dose 3.3 mg/kg), and both tumors were ablated after 75 minutes (8 rats, 15 tumors), a time chosen based on preliminary unpublished results using a range of times after injection. In all groups, monopolar RF was applied by using a 480-kHz RF generator (3E, Radionics, Burlington, Mass.), a 21-gauge non-internally-cooled electrode, and an abdominal grounding pad (B.D.W. and T.M.K). Tumors were ablated with a typical power of 2-5 watts to achieve an electrode temperature of 80° C. for two minutes.

Tumor Assessment and Histological Analysis

Rat weight and tumor sizes measured by calipers were recorded weekly for two weeks (B.D.W. and T.M.K). Tumor volume was then calculated according to the approximation $V=\frac{1}{2}ab2$, where a and b are the long and short axes of the tumor, respectively. All tumor volumes were normalized with respect to the pretreatment volume, and then tumors treated with P85 were compared to controls. After 2 weeks, rats were euthanized, and tumors were excised and fixed in 10% buffered formalin for at least 24 hrs. Fixed tissues were dehydrated, embedded in paraffin, and sliced into 5 µm sections which were subsequently stained with hematoxylin and eosin (H&E) or Masson's trichrome (MTC) stains.

Histological slides were digitized using a video microscopy system consisting of a light microscope (BX60, Olympus, Japan), video camera (DXC-390, Sony, Japan), position encoded motorized stage (ProScan, Prior Scientific, Rockland, Mass.), and software (Image-Pro with Scope-Pro, Media Cybernetics, Silver Springs, Md.). Images of the MTC slides with a 4× objective were obtained using the tiling function of Scope-Pro (Breen, M. S. et al., *Ann Biomed Eng* 33:1100-1112, 2005). For analysis, two independent observers (B.D.W and A.A.E) manually segmented and measured the visible areas of coagulation necrosis and viable tumor cells using Image J (NIH, Bethesda, Mass.), confirming the identification of each region on H&E and MTC slides in high magnification. Measurements from the two independent segmentations were averaged and used to determine coagulated area, viable tumor area, total histology area, and the percentage of the total extracted region showing coagulation necrosis. These areas were compared between groups treated with local or systemic P85 and controls. Viable tumor regions were those with cells similar to untreated cells and featuring: intact cell membranes, low degree of differentiation, high nuclear fraction, high pleomorphism, and abundance of mitotic figures. Slides where the entire extracted region appeared to be necrotic at high magnification were designated as having no viable tumor present.

Coagulation Area Measurement

To measure the acute effects of P85 administration on the size of ablation-induced coagulation, additional tumors were inoculated in 9 rats (6 tumors per group) were treated as described above for groups I-III. Rats were euthanized 24 hours after treatment, and 2 mm tumor slices were cut perpendicular to the ablation needle track and soaked with 2% 2,3,5-triphenyltetrazolium chloride (TTC) (BD Biosciences, San Jose, Calif.) for 30 min to stain tissues with intact mitochondrial activity (Goldberg S. N. et al., *Radiology* 222:797-804, 2002). Areas of the coagulated regions were then measured (B.D.W.).

Statistical Analysis

All data are presented as mean±the standard error of the mean (SEM) unless otherwise noted. Statistical tests were performed using the software package S-Plus (2005, version 7.0, Insightful, Seattle, Wash.). Cytotoxicity data were normalized with respect to controls, and analysis was then performed separately at each temperature using linear regression analysis with treatment group and time as independent variables, and two-sided Tukey-Kramer comparison was used when comparing groups. Clone formation was assessed by comparing treatment versus control at each time point and temperature using a two-sided, unpaired t-test. For the in vivo data, unpaired, two-sided t-tests were used when comparing tumor volumes, areas of viability, % coagulation necrosis, or coagulation area. Fisher's exact test was used to compare the proportion of tumors which had no detectable viable tumor. The p-value used for significance in all tests was 0.05.

Results

In Vitro Effects of P85

Figure 2:
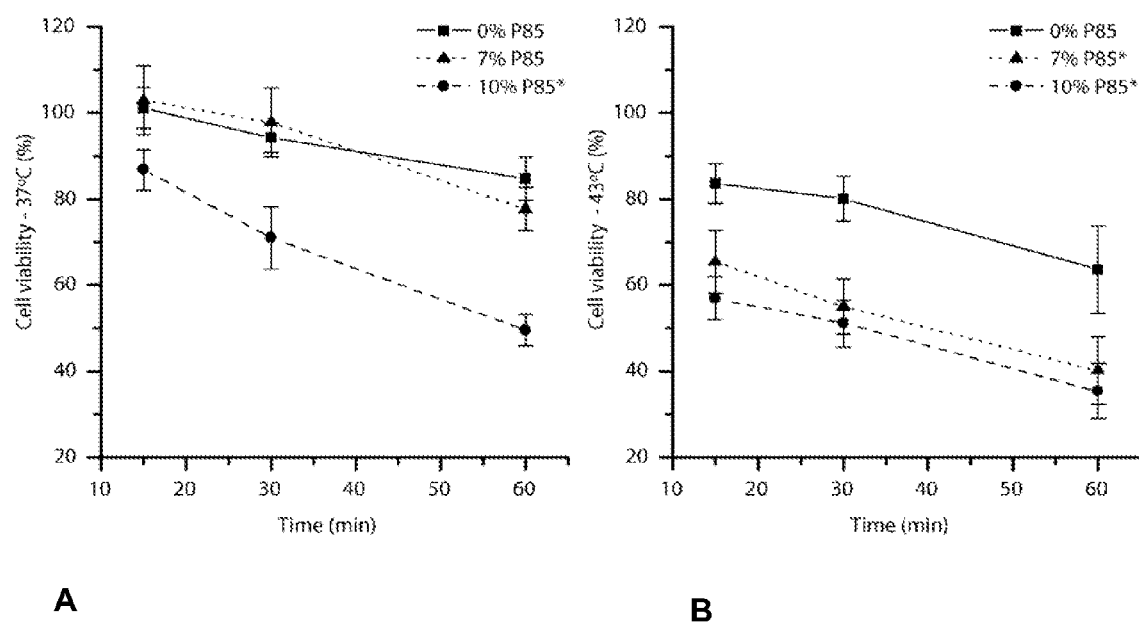
FIGS. 2A-B are a series of graphs showing the viability of DHD/K12/TRb carcinoma cells treated with three different Pluronic P85 concentrations at 37° C.

Viability as a function of time and P85 exposure is shown for two different temperatures in FIG. 2. At 37° C., viability of cells exposed to 7% P85 was comparable to that without P85, but cells with 10% P85 showed a significant loss of viability (23±5%, p=0.00002). At 43° C. all test groups experienced statistically significant toxicity due to the heat exposure. Cells treated with 7% P85 and 10% P85 were 22±5% (p=0.0002) and 28±5% ($p<10^{-5}$) less viable than controls, respectively. Importantly, while 7% P85 was not inherently toxic at 37° C., it substantially increased the toxicity of mild hyperthermia even for exposures as short as 15 minutes.

Figure 3:
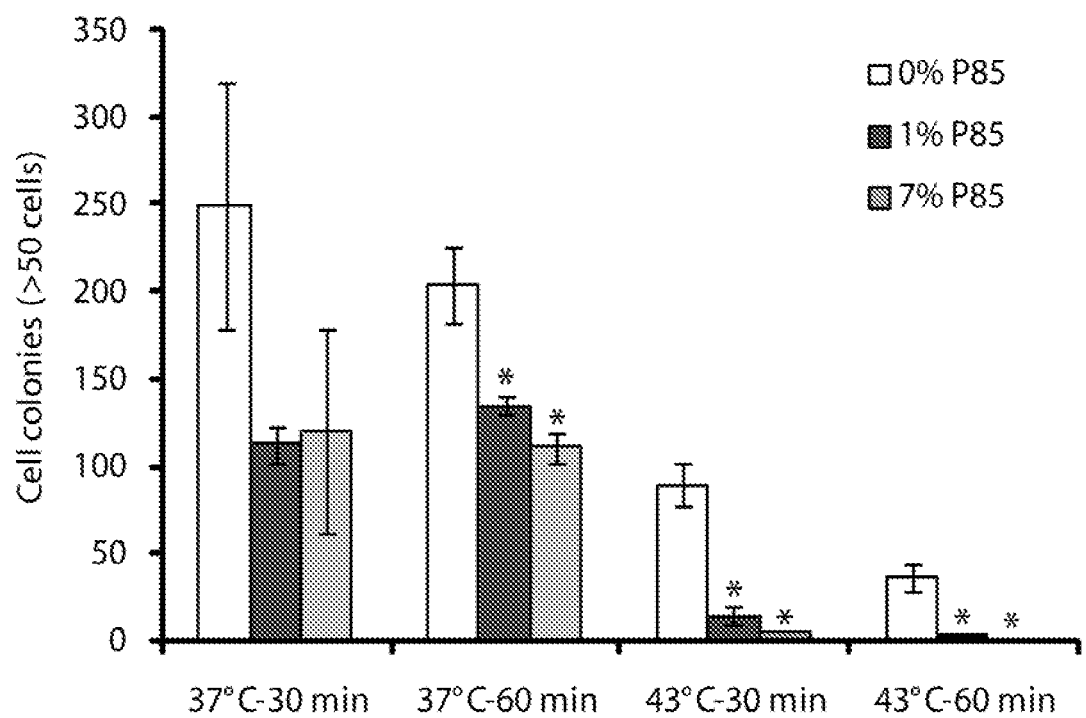
FIG. 3 is a histogram showing the proliferation ability of DHD/K12/TRb carcinoma cells treated with 1% or 7% P85 versus controls at 37° C. and 43° C. Each measurement is the mean of 3 plates±SEM, and (*) indicates the treatment is significantly different from control at that temperature exposure.

Clonogenic measurement of cell proliferative activity confirmed the effects of P85 in sensitizing the cells to heat exposure (FIG. 3). After 60 minutes of exposure at 37° C., cells treated with 1% and 7% P85 formed 33±10% (p=0.04) and 46±10% (p=0.02) fewer colonies than controls, showing some loss of proliferative activity even without exposure to heat. However, cells treated with 1 and 7% P85 at 43° C. lost even greater fractions of their replicative ability, 92±17% (p=0.01) and 100±17% (p=0.008), respectively. The combination of P85 and mild heat exposure inhibited colony formation substantially more than either component alone.

Tumor Growth Suppression

Figure 4:
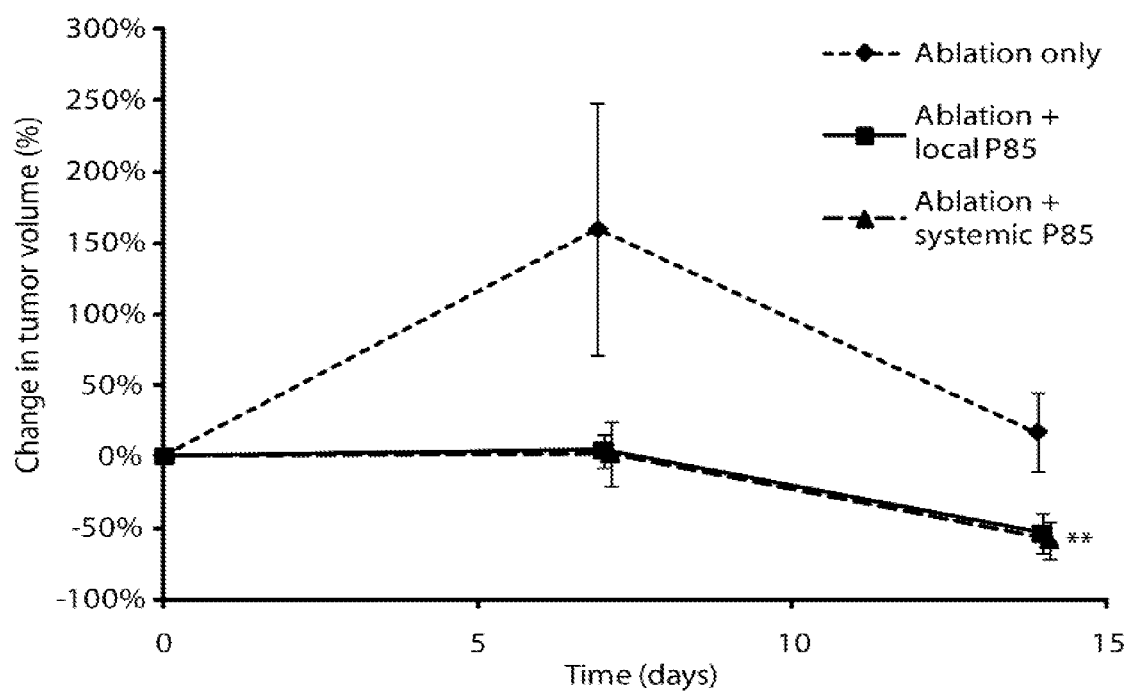
FIG. 4 is a graph showing the progression of tumor volume for the in vivo treatment groups over 14 days. Volume change is shown as a percentage of pretreatment tumor volume. Error bars depict the SEM, and (**) indicates that both local and systemic P85 volumes are significantly different that ablation alone.

Tumors had a pretreatment diameter of 8.9±0.5 mm, with no significant difference in size between groups. Seven days after treatment, tumor volume increased 159±17% in the control group (FIG. 4). However, the volume of tumors treated with P85 before ablation remained unchanged relative to the original tumor volume (local P85, 3±12%; systemic P85, 1±23%). By day 14, the volume of the ablation only tumors decreased to near the original tumor volume (16±28%), but in both Pluronic pretreatment groups the tumor volume had decreased by more than half (local P85, −55±14%; systemic P85, −59±14%). At day 14, the differences were statistically significant between the control and both P85 pretreatment groups (local P85, p=0.03; systemic P85, p=0.02).

Histological Analysis

Quantitative histological analysis of explanted tumor tissue was used to assess the pathological outcome of the tumors and is summarized in Table 1.

TABLE 1

Summary of quantitative histology analysis

| | Ablation only | Local P85 | Systemic P85 |
|---|---|---|---|
| No viable tumor present | 4/14 (29%) | 3/13 (23%) | 7/15 (47%) |
| Mean viable tumor area (cm$^2$) | 0.33 ± 0.11 | 0.11 ± 0.02 | 0.07 ± 0.03* |
| % coagulation necrosis | 61 ± 9% | 52 ± 8% | 79 ± 7%** |

*indicates significant difference from ablation only
**indicates significant difference from local P85

Figure 5:
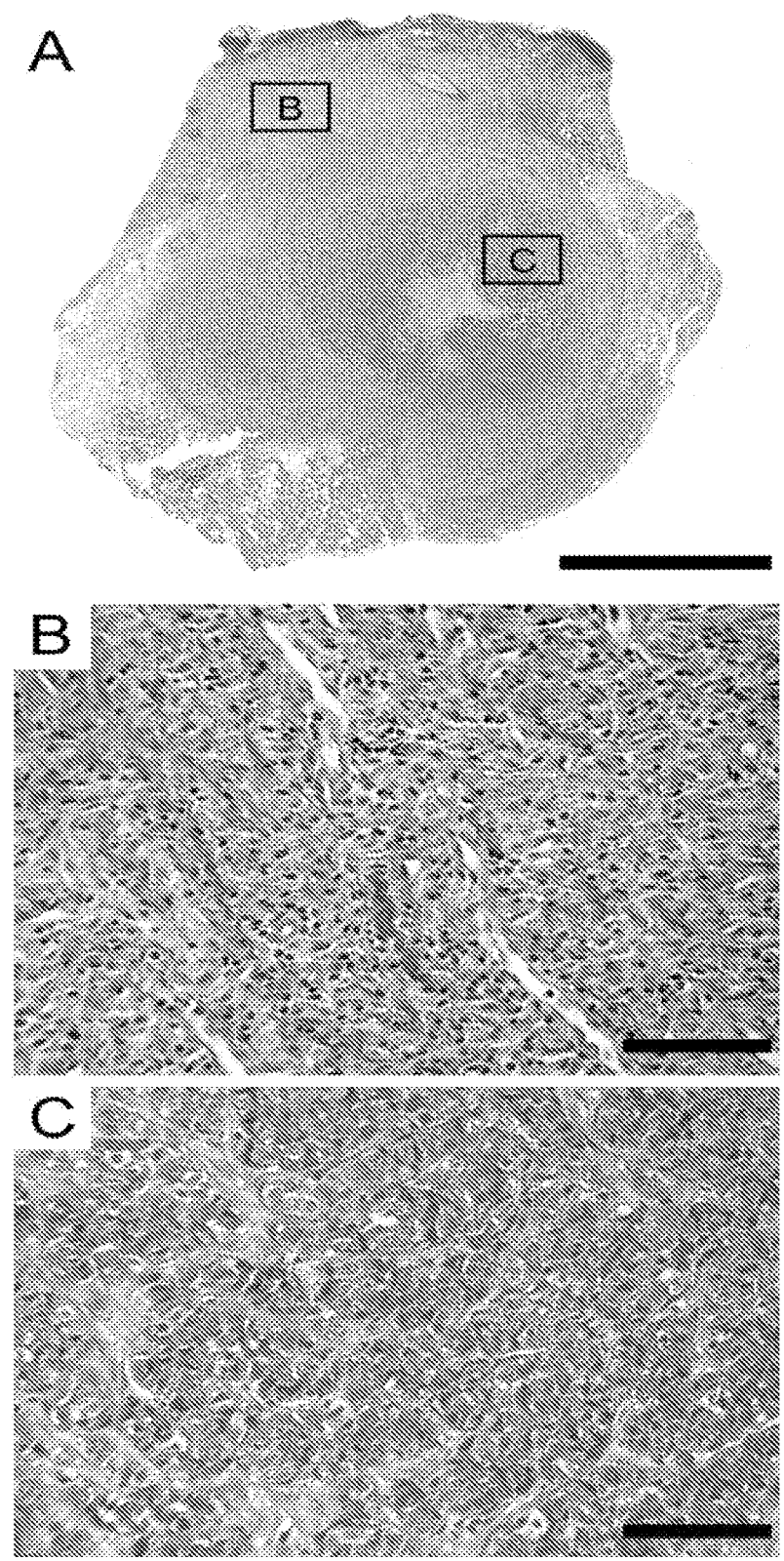
FIGS. 5A-C are a series of photographs showing representative Masson's trichrome (MTC) stained section with residual tumor cells 14 days after RF ablation.
Figure 6:
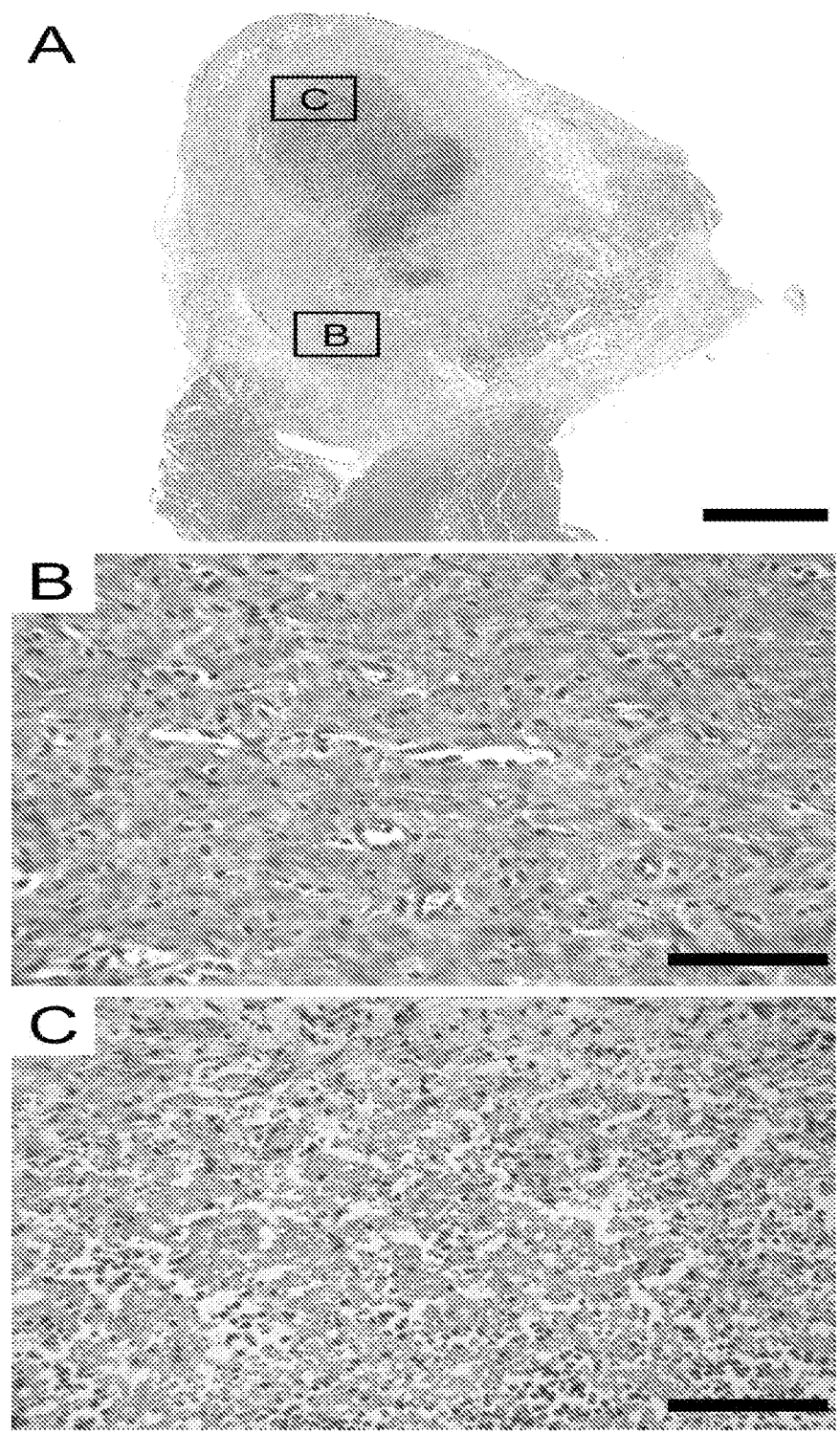
FIGS. 6A-C are a series of photographs showing representative Masson's trichrome (MTC) stained section with residual tumor cells 14 days after RF ablation.

Histology from the three groups could be categorized into two types: sections containing no viable tumor and sections containing residual viable tumor nodes. The number of sections with no viable tumor present was similar in the ablation only (4/14, 29%) and local P85 groups (3/13, 23%, p=0.65), and was higher but not statistically significant in the systemic P85 group (7/15, 47%, p=0.26). Histologic sections containing viable tumor exhibited a similar pattern throughout the three groups, and a representative section is shown in FIGS. 5A-C. These sections were characterized by two main differentiable regions: coagulation necrosis and viable untreated tumor. In contrast, sections containing no residual viable tumor cells consisted of a single large ablated region as shown in FIGS. 6A-C.

The size of the coagulated area on the day 14 histology was largest in the control group, but the differences with local P85 (p=0.06) and systemic P85 (p=0.28) were not significant. Mean viable tumor area was highest in the ablation only group and lower in both P85 groups, although this difference was significant only for ablation only versus systemic P85 (p=0.02). Additionally, the percent of the resected tissue scored as coagulated in the systemic P85 group was significantly higher than that from intratumoral P85 (p=0.02), although not statistically different from control (p=0.12).

Effects on Coagulation Area

Figure 7:
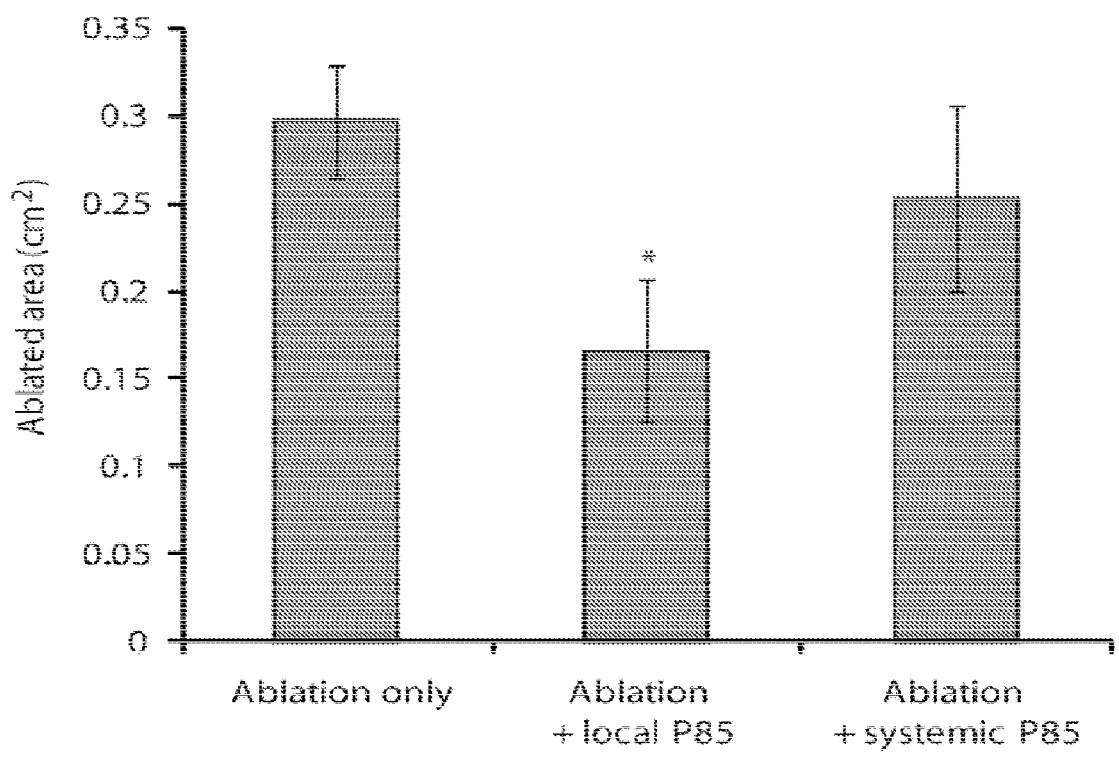
FIG. 7 is a histogram showing the area of coagulation necrosis measured from TTC stained tissue sections 24 hours after the ablation. Error bars show the SEM, and (*) indicates the treatment is significantly different from ablation only.

Areas of coagulation necrosis determined from TTC stained sections 24 hours after the treatment are shown in FIG. 7. The coagulated areas in the ablation only (0.30±0.03 cm2) and systemic P85 (0.25±0.05 cm2) tumors were similar. However, coagulated area in the local P85 group (0.17±0.05 cm2) was reduced by 44% relative to control (p=0.03).

Discussion

Recent technological developments, such as internally-cooled or multi-tined expandable electrodes (Buscarini, E. et al., *Eur Radiol* 14:31-37, 2004), the use of imaging guidance and treatment assessment (Lewin, J. S. et al., *J Magn Reson Imaging* 8:40-47, 1998), and saline coadministration (Livraghi, T. et al., *Radiology* 202:205-210, 1997), have further increased the scope of tumors that can be treated with RF ablation. Nonetheless, peripheral cooling of tumor tissue near major blood vessels, restricted size of energy deposition, and seeding of residual tumor around the needle electrode track have all been shown to be causes of incomplete treatments leading to local tumor re-growth, particularly in larger tumors (Solbiati, L. et al., *Eur J Ultrasound* 13:149-158, 2001; Tateishi, R. et al., *Cancer* 103:1201-1209, 2005).

Several studies have reported the use of pharmacological agents as adjuvants to RF ablation in an attempt to increase treatment volumes and improve clinical outcomes. Goldberg et al. described the benefits of coadministration of liposomal doxorubicin (Doxil) by intratumoral or IV injection with ablation (Goldberg, S. N. et al., *Radiology* 797-804, 2002; Goldberg, S. N. et al., *Radiology* 220:420-427, 2001). Both methods showed increased tumor necrosis, but IV liposomes appeared more promising because they resulted in increased necrosis at the tumor periphery, where tumors are more likely to recur. In the only patient trial in 2002, 10 patients given IV Doxil before ablation demonstrated increased necrosis in perivascular and peripheral tumor sites 2-4 weeks after treatment (Goldberg, S. N. et al., *AJR Am J Roentgenol* 179:93-101, 2002). Another experimental study by Haaga et al. demonstrated that 5-fluorouracil impregnated polyanhydride implants along with RF ablation led to improved tumor treatment response compared to RF alone in a rabbit liver cancer model (Haaga, J. R. et al., *Radiology* 237:911-918, 2005). These results underscore the potential to maximize the effects of RF ablation by supplementing it with systemically or locally administered pharmacological agents.

Pluronics are nonionic, triblock copolymers composed of blocks of ethylene oxide (EO) and propylene oxide (PO) with a generic structure of $EO_a$-$PO_b$-$EO_a$, where a and b are the number of repeats of each unit. These polymers are not inherently toxic at active concentrations and have been used to solubilize and deliver hydrophobic drugs within micelles (Kabanov, A. V. et al., *J Control Release* 82:189-212, 2002; Batrakova, E. V. et al., *Br J Cancer* 74:1545-1552, 1996). Despite their lack of inherent toxicity, Pluronics have been shown to sensitize cancer cells to chemotherapy (Kabanov, A. V. et al., *J Control Release* 91:75-83, 2003) based on several mechanisms, including: reducing activity of cell detoxification systems (such as p-glycoprotein and glutathione sulfhydryl), depleting intracellular ATP concentration, reducing expression of anti-apoptotic genes, and changing cell membrane fluidity (Alakhov, V. et al., *Bioconjug Chem* 7:209-216, 1996; Batrakova, E. V. et al., *Br J Cancer* 85:1987-1997, 2001). These effects occur at relatively low Pluronic concentrations below the critical micellar concentration (CMC), which is the concentration of polymer above which individual polymer molecules associate into micelles, or spherical supermolecular aggregates. For this reason, the cellular effects are believed to be due to unimers rather than micellar aggregates. Pluronic P85, with an EO repeat length of 26 and PO repeat length of 40, is particularly suitable to induce these effects because of its balance between relatively high hydrophobicity and intermediate CMC ($6.5 \times 10^{-5}$ M), which allows for a high concentration of unimers (Batrakova, E. et al., *Pharm Res* 16:1373-1379, 1999). Most recently, P85 was found to increase the cytotoxicity of carboplatin in the cell line used in our study (Exner, A. A. et al., *J Control Release* 106:188-197, 2005). The negligible systemic toxicity of P85 combined with its wide range of biological activity make this surfactant an ideal thermosensitizer for use with RF ablation.

Our study examined the use of P85 as a thermosensitizer prior to RF ablation treatment of experimental tumors. While previous work has successfully supplemented RF ablation with various cytotoxic agents (Goldberg, S. N. et al., *AJR Am J Roentgenol* 179:93-101, 2002; Goldberg, S. N. et al., *Radiology* 220:420-427, 2001; Goldberg, S. N. et al., *AJR Am J Roentgenol* 179:93-101, 2002; Haaga, J. R. et al., *Radiology* 237:911-918, 2005; Hines-Peralta, A. et al., *Radiology* 240:82-89, 2006), to the best of our knowledge our study is the first attempt to establish an ablation protocol that utilizes a nontoxic agent to increase cellular susceptibility to heat related injury while minimizing systemic side effects of drugs. Experiments were carried out to demonstrate the feasibility of this approach both in vitro under in a cell culture environment and in vivo in an animal model. In vitro, cells were exposed to mild hyperthermia ranging from 15-60 minutes at 43° C. to simulate heat doses that might be experienced by tumor cells at the outer periphery of the ablated region (Johnson, P. C. et al., *Ann Biomed Eng* 30:1152-1161, 2002). This heat exposure combined with P85 was shown to decrease both the mitochondrial enzyme activity (and thus viability) and proliferative ability of a rat colorectal carcinoma cell line. This finding is important because it represents a vital first step in developing compounds that can increase the toxicity of heat without substantial toxicity to normal cells.

In vivo, tumors treated with either intratumoral or systemic P85 before ablation had reduced volumes compared to control on days 7 and 14. The large increase in control tumor volume on day 7 may result from inflammation and edema associated with the resolving ablated tissue, which appears to be reduced in tumors treated with P85 and ablation. It is possible that P85 has an effect on the extent of post-ablation inflammation which would explain why the P85 treated groups are smaller on day 7. By day 14, both P85 treatment groups showed a substantially reduced volume at day 14 compared to ablation alone, indicating that it may be possible to extend the thermosensitization effects of P85 to tumor treatment strategies. One notable difference between the two pretreatment strategies was that tumors treated with intratumoral P85 had a smaller percentage of necrosis on histological sections compared to tumors treated with systemic P85. Furthermore, the local P85 group had the smallest area of coagulation necrosis on histology. This finding is supported by the TTC assay, where smaller areas of necrosis were seen in the local P85 group 24 hours after ablation. The explanation for the different coagulation sizes in this study is not clear. It is possible that the intratumoral injection of polymer interferes with tissue heating by either insulating the surrounding tumor or provides an alternate path for RF-induced current. In contrast, the size of the TTC-demarcated coagulated region after 24 hours was similar for the systemic P85 and ablation only groups. Thus, the difference between tumor volume in ablation only and systemic P85 after 14 days is not likely to be explained by short-term changes in the coagulated region. These results suggest that P85 does not immediately increase the size of the region destroyed by ablation but instead contributes to slow cellular processes which take place over a period of several days. Because the effects of P85 on the inflammatory response to ablation are unknown, the best measurable outcome on histology is the gross amount of viable tumor on day 14, which is least in the systemic P85 group. To our knowledge, our work is the first to demonstrate the thermosensitizing effects of Pluronic P85 both in vitro and in vivo. While the exact mechanism is unknown, several previously established effects could be relevant. First, ATP depletion could decrease the ability of heat damaged cells to recover from sublethal injury, like that occurring at the outer boundary of the ablated region. Second, altered gene expression, such as a decrease in anti-apoptotic or heat shock proteins, could increase the number of affected cells undergoing apoptosis in the days following the treatment. Third, the copolymer may disrupt the cell membranes, leaving them more vulnerable to heat damage.

Although the results from our study are promising, they are not without limitation. First, the results are based on effects after two weeks, but earlier histology time points, such as four or eight days, could provide more information on the exact mechanism of these effects. Second, this effect was established only in a single cell line and tumor model, and may not be universally applicable. Future study in additional cell and tumor types could supplement these results. Third, no temperature mapping was performed in this study, which limits the conclusions that can be drawn about effects in specific temperature conditions. Experiments that correlate temperature exposure with cell death could provide much more detailed information about how and where P85 exerts its effects.

Pluronic P85 increased the cytotoxic effects of hyperthermia on cancer cells, both in vitro when cells were exposed to mildly elevated temperatures (43° C.) and in vivo in the context of RF ablation of experimental tumors. Our study establishes the potential for using a thermosensitizer, particularly Pluronic P85, to improve the therapeutic outcome of tumor RF ablation. Such knowledge can lead to more in depth exploration of the effects and mechanisms of using a thermosensitizer and ultimately to improvement of the best available clinical care for minimally invasive tumor treatment.

Example 2

Materials and Methods

PLURONIC P85 was generously donated by BASF (Shreveport, La.). The DHD/K12/TRb rat colorectal carcinoma cell line was donated by the laboratory of Dr. W. G. Pitt, Brigham Young University (original source was the European Collection of Cell Cultures), and the Glio36Δ5 Luciferase transfected cell line was kindly provided by the laboratory of Dr. James Basilion, Case Western Reserve University). Cell culture supplies including trypsin-EDTA, Dulbecco's phosphate buffered saline, RPMI 1640 (with L-glutamine), and penicillin-streptomycin, were purchased from GIBCO (Grand Island, N.Y.). Fetal bovine serum (characterized) and Puromycin were purchased from Hyclone (Logan, Utah). The Rapid Cell Proliferation Kit was obtained from ONCOGENE (La Jolla, Calif.). Dulbecco's Modified Eagle's Medium and Hygromycin were purchased from Invitrogen (Invitrogen, Carlsbad Calif.). Sterile 0.22-μm syringe-driven filter units (Millex-GP) and CellTiter-Glo luminescent ATP assay was purchased from Promega (Madison, Wis.). Costar 96-well, flat bottom, tissue culture treated, opaque walled plates were purchased from Fisher Scientific (Pittsburgh, Pa.). May-Grunwald and Giemsa stains were obtained from Sigma-Aldrich (St. Louis, Mo.).

DHD/K12/TRb

This cell line originated from a 1,2-dimethylhydrazine-induced colon adenocarcinoma in BDIX rats, has the advantages, i.e., being able to be propagated both in vitro and in vivo (Exner, A. A. et al., *J Control Release* 106:188-197, 2005). Cells were maintained in completed RPMI medium, with 10% FBS and 1% penicillin/streptomycin. Upon reaching 70% confluence, the cells are propagated.

Luciferase Transfected Glio36Δ5

To generate human malignant glioma cells stably expressing luciferase (gli365-luc), the firefly Luc2 gene was removed from the pGL4.13 [SV40/luc2] vector (Promega) by restriction digest and inserted into the multiple cloning site of the pcDNA3.1+ vector (Clonetech) using the Roche Rapid DNA Ligation Kit. DNA was isolated from DH5α cells using the Qiagen MAXI Prep Kit and transfected by electroporation (Bio-Rad GenePulser XceII) into the Gli365 cells. The cells were maintained in Dulbecco's Modified Eagle's medium completed with 10% FBS, 1% penicillin/streptomycin, 1 μg/mL Puromycin and 240 μg/mL hygromycin.

Formulation of Test Solution

Pluronic P85 in the paste form was added to RPMI at concentrations of 0, 0.3, 1, 10, 30, 50 and 70 mg/mL and placed under refrigeration (4° C.) until dissolved (about 24 hrs). Solutions were filtered with a sterile 0.22 μm syringe filter (Millex TM-GP, Millipore, Billerica, Ma.) and stored at 4° C. until use.

Cell Treatment

One day before treatment, cells were detached with trypsin-EDTA, resuspended in RPMI or DMED, and plated into a flat bottom tissue culture treated 6-well plate or either transparent or opaque walled 96-well plates at 105 cells/mL (240 μL/well for 96-well plate and 3.2 mL for 6-well plate). The plates were placed in the incubator to allow cell adhesion.

After 24 hrs, cells were exposed to P85 test solutions (50 μL for 96-well plate and 1.2 mL for 6-well plate) for a time period between 0 to 360 min at 37° C. in the incubator. Some plates of cells received an additional exposure to P85 test solutions for a time period between 0 to 45 min at 43±0.05° C. Then cells were washed with appropriate completed medium (room temperature) twice, and assay assessment was performed either immediately or 24 hrs after treatment. In these studies, each treatment condition was repeated on at least 3 independent plates, and at least 4 wells/plates.

Cell Viability Assessment Through Intracellular ATP

Cell viability was masured with a luminescent cell viability assay (CELLTITER GLO, Promega). This assay has the advantage of 1) adding of a single reagent without the necessity of cell washing or removal of serum supplemented medium, 2) can measure not only the viability of the cells but also provide information on levels of intracellular ATP directly. Briefly, plates were removed from the incubator, and left to equilibrate to room temperature for 30 min. Then, an appropriate amount of the assay reagent was added to the wells. Cell lysis was promoted by shaking the plate for 2 min. Finally, luminescence was recorded with a TECAN US infinite 240 system with the software iControl (Durham, N.C.) and an integration time of 500 ms.

Clonogenic Survival

After treatment, DHD/K12/TRb cells from the 6-well plates were detached with 0.25% of trypsin-EDTA, and washed twice with completed RPMI. The cells were reseeded in 24-well flat bottom cell culture treated plates at 700 cells/ mL (800 μL/well). This concentration was selected according to an optimization study done on untreated cells, which ensures normal cell proliferation but allow for distinguishable colony formation without forming a single confluent cell monolayer. Cells were allowed to grow for 9 days. After 3 min of methanol fixation, and 5 min May-Grunwald and 10 min Giemsa stains, all colonies in each well were counted manually by two individuals. A single colony w defined as a group of viable cells that has cell number that is greater or equal to 50.

Cell Viability Assessment Through Mitochondria Enzyme Activity

Cell viability was evaluated using a mitochondrial enzyme activity assay in which a mitochondrial dehydrogenase cleaves the tetrazolium salt, WST-1, and releases formazan. In this assay, the activity of mitochondrial dehydrogenase is directly proportional to cell viability. The assay was performed following manufacturer directions. Briefly, cell supernatant from each 96-well plate was aspirated, while reagents provided by the manufacturer were diluted with the completed cell medium. Then 100 μL of the diluted reagents was added to each well. The plates were then kept for 1 hr at room temperature, and the optical density was determined at λ=450 nm using the micro plate reader (ELx808, Bio-Tek, Winooski, Vt.).

Statistical Analysis

For all studies, untreated controls at 37° C. were utilized for data standardization. Briefly, data collected from untreated control cells were averaged, and this value was being defined as 100%. Then all values from each well under each of the treated groups were divided by this value to obtain a percentage of the untreated control. Finally, a two-tailed, unpaired Student's t-test was performed for all the standardized data. For multiple comparisons, significance levels were corrected using a Bonferroni adjustment. All data is represented as mean±SEM (standard error of mean). P value of less than or equal to 0.05 is considered to indicate a significant difference before Bonferroni correction.

Results

Throughout the text the following phrases are used interchangeably: acute P85 refers to 15 min P85 exposure at 37° C.; acute P85 under heat specifies treatments receiving 15 min P85 exposure at 43° C.; long-term P85 denotes 240 min P85 exposure at 37° C.; and combination of P85 preexposure with heat implies treatments of 240 min P85 exposure at 37° C. with an additional 15 min at 43° C.

DHD/K12/TRb Rat Colorectal Adenocarcinoma Cell Line

Effect of Sub-Lethal Heat on Cell Viability

Figure 8:
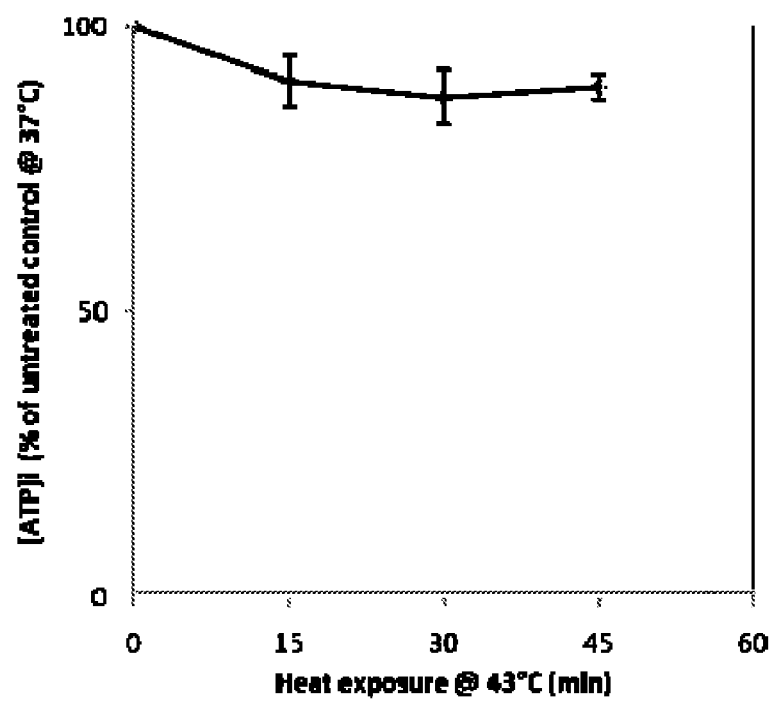
FIG. 8 is a graph showing the change in cell viability (intracellular ATP) in DHD/K12/TRb cells in response to heat at 43° C. for 15, 30, 45 minutes and 24 hours after treatment (n=12). * indicates statistical significant difference compared to untreated control (Mean±SEM)

When cells were exposed to heat alone at 43° C. for 15, 30 and 45 min, little intracellular ATP changes were observed 24 hrs after treatment (FIG. 8). 90.4±4.5% of intracellular ATP was detected when cells were exposed to heat for 15 min. Although an additional 30 min of heat exposure caused little change in intracellular ATP (81.4±2.1%) compared to untreated controls, differences were significant.

Figure 9:
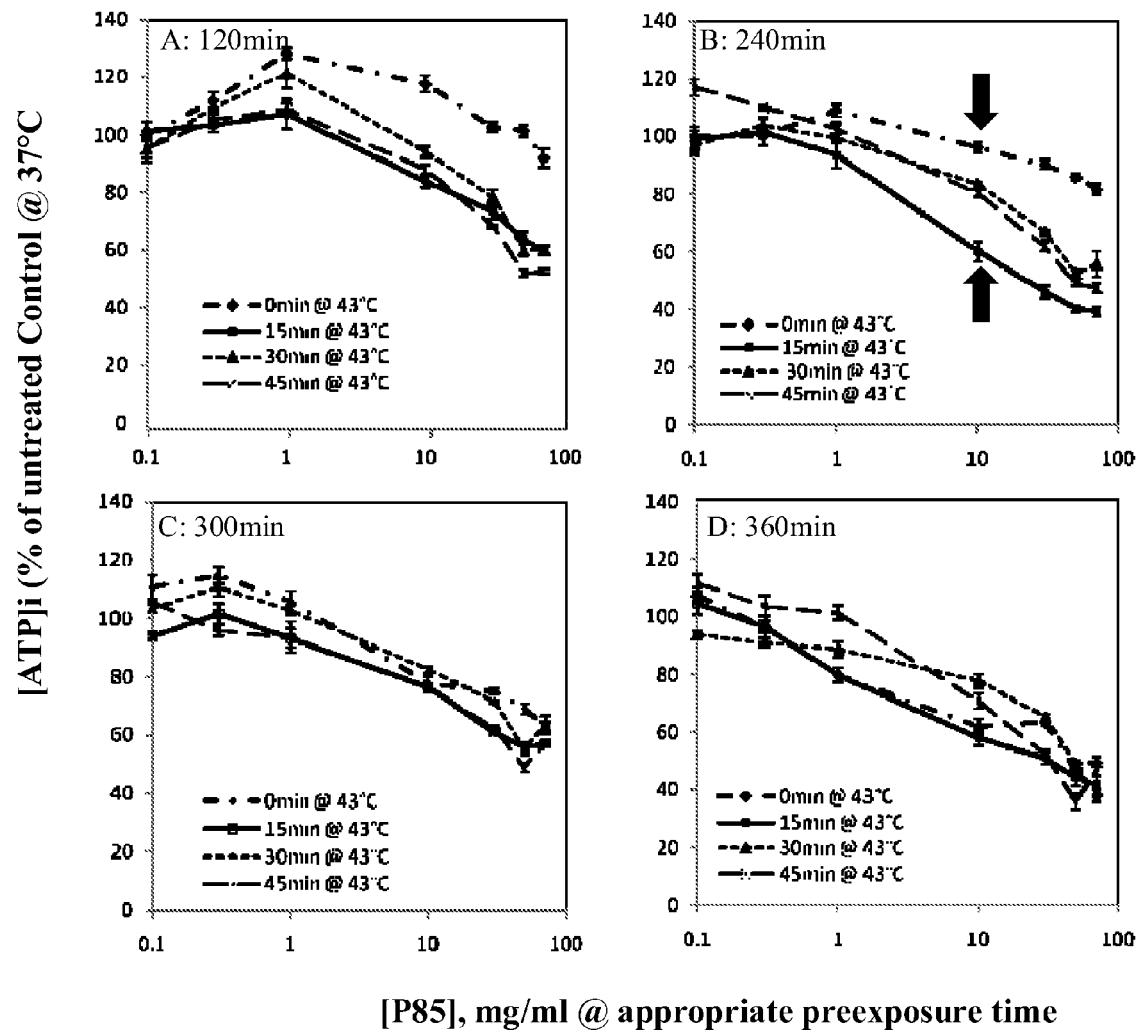
FIGS. 9A-D are a series of graphs showing changes in cell viability (Mean±SEM) with respect to untreated control. Statistical significant difference were detected between combination of P85 pre-exposure with heat vs. long-term P85 (P=6.56E-10), between combinations of P85 pre-exposure with heat vs. heat alone (P=3.34E-07), between combination of P85 pre-exposure with heat vs. no treatment control (P=8.02E-11)

P85 Dose, Pretreatment Time, and Heat Exposure Time on Levels of Intracellular ATP:

The effect of P85 pre-exposure prior to heating for 0-45 minutes at 43° C. was examined. Assays were performed 24 hrs after treatment. Considerable differences were noted between low (0.3-1 mg/mL) and high (10-70 mg/mL) doses of P85 as well as pre-exposure duration and heating time. Low dose P85 alone (37° C., n=12) led to an elevation of intracellular ATP up to 30% above baseline control when cells were pre-exposed to P85 for 120-360 min at 37° C. and showed no influence on cell viability (FIGS. 9A-D). In contrast, P85 dose of 10-70 mg/mL (n=12) decreased ATP for all but 120 min pre-exposure. For this group, least effect on viability was observed at 10 mg/mL. Most notably, after 360 min of exposure, the ATP levels were markedly reduced to 38.1±2.3% (n=21) for a dose of 70 mg/mL (FIG. 9D) suggesting time and dose dependent toxicity of P85. Once cells were pre-exposed to P85 at 37° C., an additional 15 min exposure at 43° C. was sufficient to induce a reduction in viability (n=24); further heat exposure of up to 45 min was found to be of no added benefit. Optimal sensitization was observed when cells were pre-exposed to 10 mg/mL of P85 for 240 min at 37° C. (FIG. 9B). Detailed data are presented under FIG. 12A.

Figure 10:
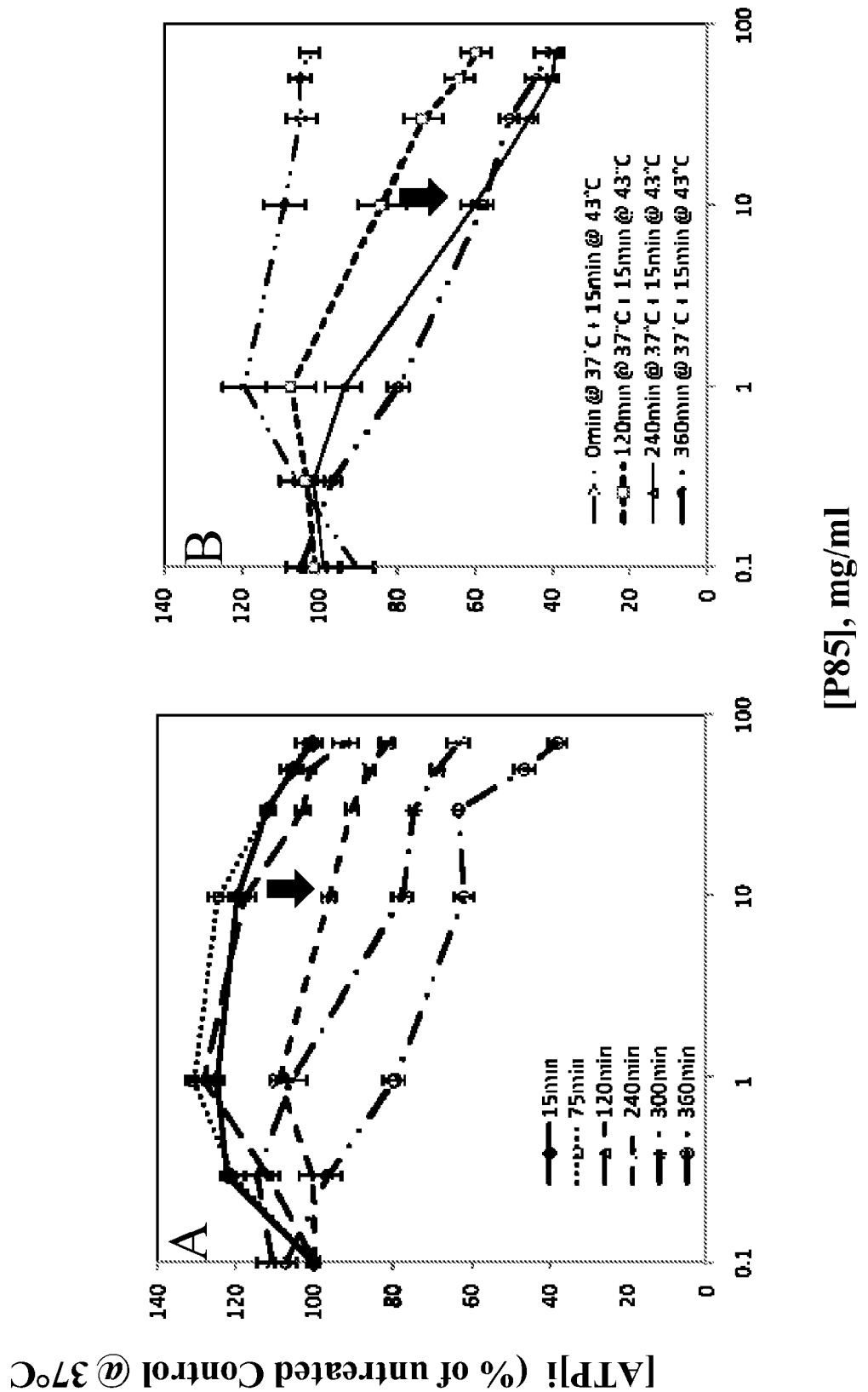
FIGS. 10A-B are a series of graphs showing the effect of P85 dose, pre-exposure time, and hyperthermia duration on cell viability (Mean±SEM). Data presented as percent of intracellular ATP (cell viability) of untreated control.

FIGS. 10A-B further illustrates that P85 at low concentrations and short pre-exposure times primarily increases intracellular ATP in DHD/K12/TRb cells. However, at higher concentrations or longer pre-exposure times, P85 becomes toxic to the cells. When 10 mg/mL of P85 pre-exposed to cells for 240 min at 37° C., no change in levels of intracellular ATP was detected (FIG. 10A). Once 15 min of further exposure was applied under heat, ATP level was depleted to 60% (FIG. 10B).

Clonogenic Cell Survival:

Treatment conditions of 240 min P85 pre-exposure at 37° C. with an additional 15 min exposure at 43° C. were selected as optimal for testing whether 1) ATP depletion caused by P85 plus heat was a transient effect which would not cause permanent cell injury, or 2) P85 plus heat could inhibit the ability for cell colony formation. Heat alone for 15 min has reduced the number of colonies from 193.0±5.4 to 105.0±27.7 (FIG. 11A). Yet, the acute P85 exposure did not cause further reduction in number of cell colonies (208.0±8.0, 222.0±7.0, 197.0±41.0, 195.0±35.0, and 183.0±42.0 at 0.3, 1, 10, 50 and 70 mg/mL of P85, respectively) compared to 15 min of heat alone (FIG. 11A). In contrast, combination of P85 pre-exposure with heat significantly reduced the number of cell colonies at low concentrations of P85 (from 155.0±17.0 to 42.0±7.0 at 0.30 mg/mL, 49.0±7.0 to 10.0±1.0 at 1 mg/mL, and 29.0±9.0 to 0.7±0.7 at 10 mg/mL of P85). While complete eradication was achieved at higher concentrations of P85 with heat (FIG. 11B); cells receiving long-term P85 exposure alone showed signs of survival even at high concentrations of P85 (6.0±2.9 at 50 mg/mL and 6.0±1.5 at 70 mg/mL). All results for colony formation are based on repetition of 3. Statistically significant differences were noted between heat alone vs. combination of P85 pre-exposure with heat (5.37E-06<P<1.56E-03), as well as between untreated control vs. combination of P85 pre-exposure with heat at all concentrations of P85 (9.53E-04<P<2.31E-03).

Changes in Intracelluar ATP Immediately after Treatment

Immediately after treatment all conditions showed significantly increased levels of intracellular ATP in DHD/K12/TRb cells compared to untreated control (8.15E-13<P<1.54E-06). Long-term P85 exposure caused an increase up to 182.0±3.8% (n=12), heat alone caused an increase up to 150.0±1.7% (n=8) and combination of P85 pre-exposure with heat caused an increase up to 158.0±3.3% (n=16). However, acute P85 at 43° C. for 15 min (n=12) increased ATP to the highest level, 219.0±3.4% of untreated control (FIG. 12A), which is statistically significantly different compared to all other treatment conditions (1.04E-12<P<2.44E-07).

Changes in Mitochondrial Enzyme Activity Immediately after Treatment

Figure 12:
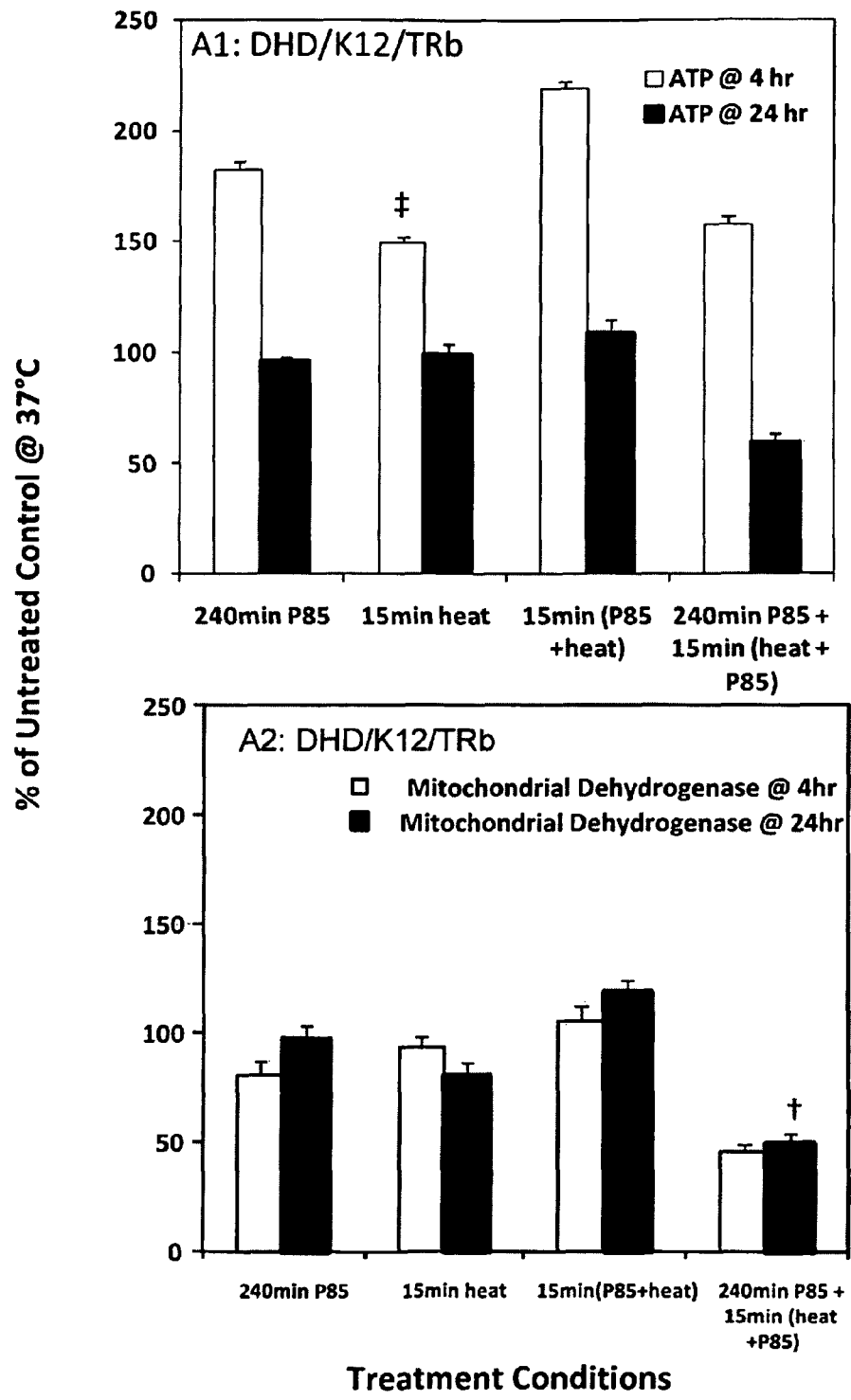
FIGS. 12A-B are a series of graphs showing cell viability of DHD/K12/TRb cells and Glio36Δ5 cell lines under P85 (acute or long-term) and/or heat treatment immediately or 24 hrs after treatment (Mean±SEM). ‡ implies statistically significant differences vs. acute P85 under heat immediately after treatment; § indicates significant differences vs. combination of P85 pre-exposure with heat 24 hrs after treatment; * denotes significant differences vs. combination of P85 pre-exposure with heat immediately after treatment; † specifies significant differences vs. acute P85 under heat 24 hrs after treatment.
Figure 12:
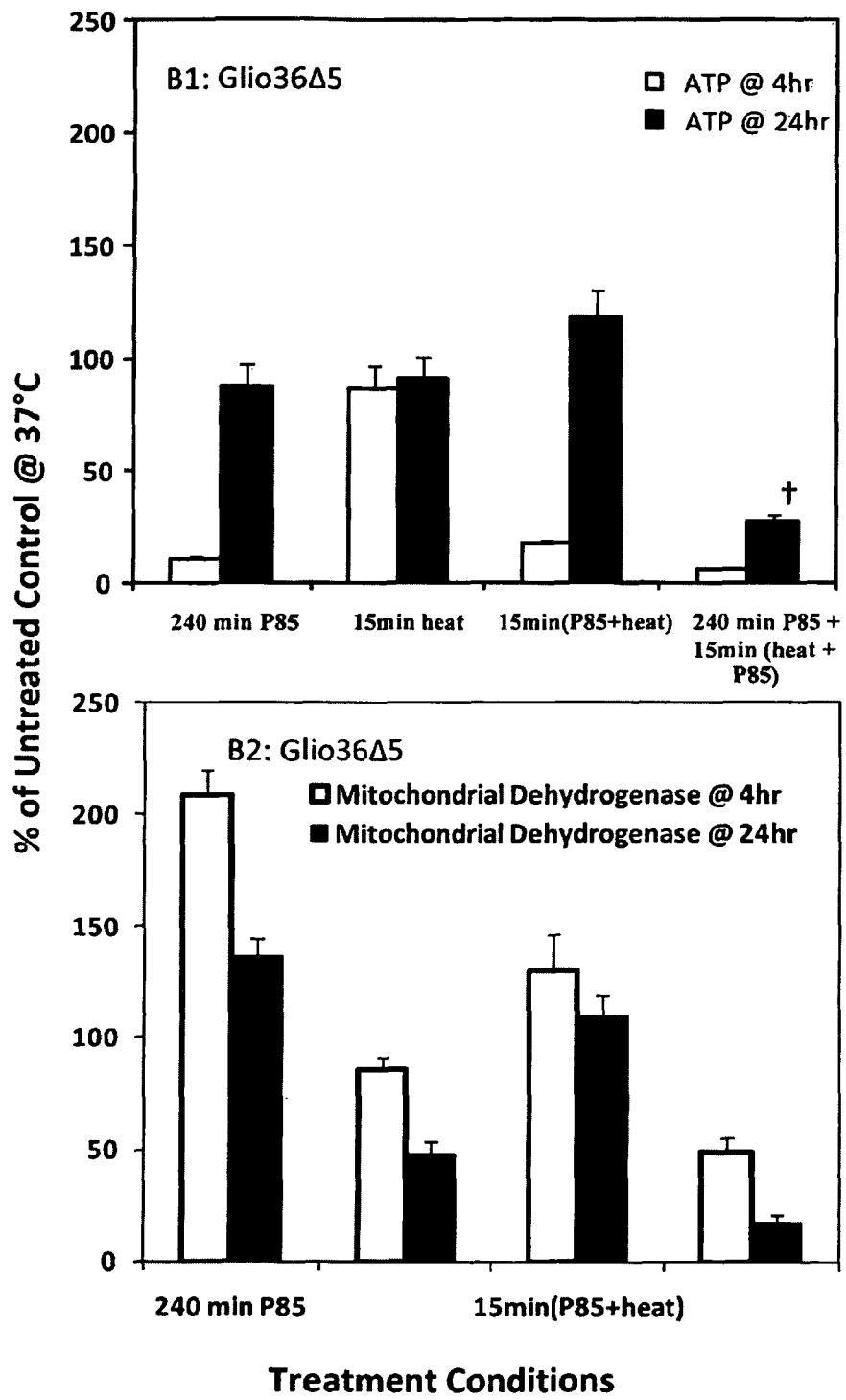

Compared to untreated control, only the combination of P85 pre-exposure with heat caused a significant decrease in cell viability (mitochondrial dehydrogenase activity) immediately after treatment (P=1.24E-06). Statistically significant differences were also noted between combination of P85 pre-exposure with heat and all the other treatment conditions (4.11E-04<P<1.10E-07). Long-term P85 exposure caused a decrease in cell viability to 81.0±6.7%, while combination of P85 pre-exposure and heat caused it a decrease to 45.4±5.1%. Heat alone and acute P85 under heat caused negligible changes in mitochondrial enzyme activity (FIG. 12B, n=12).

Changes in Intracellular ATP Twenty Four Hours after Treatment

Following a 24 hour period after treatment, cells receiving long-term P85 (n=12), heat alone (n=12) or acute P85 at 43° C. (n=12) showed a significant degree of recovery in cellular metabolism (to 96.2±1.8%, 98.8±4.5%, and 109.0±5.5% or untreated control). In contrast, cells which received combination of P85 pre-exposure and heat (n=24) failed to recover and showed intracellular ATP at 60.1±3.5% of control (FIG. 12A). These levels are significantly lower than all treatment conditions including untreated control (1.38E-10<P<1.76E-05).

Mitochondrial Enzyme Activity Twenty Four Hours after Treatment

With the exception of cells receiving long-term P85 exposure (96.7±5.8%), all other treatments showed significantly different levels of viability compared to untreated control (7.20E-16<P<1.73E-02). While heat alone and combination of P85 preexposure with heat decreased viability to 80.4±5.0 and 49.1±3.5%, respectively, acute P85 with heat increased viability to 118.0±6.6% of untreated control (FIG. 12B, n=12). Once more, significant differences were observed between P85 pre-exposure and heat compared to all other treatment conditions (1.35E-12<P<3.25E-06). Significant differences between acute P85 under heat and all the other treatment conditions (1.35E-12<P<1.67E-02) were also noted.

Luciferase Transfected Glio36Δ5 Cell Line

Percent of Intracellular ATP Immediately after Treatment

Significant amount of intracellular ATP was depleted following exposure to P85 regardless of duration. Cells were treated with long-term P85 exposure (10.7±0.7%), acute P85 under heat (17.7±3.9%), or combination of P85 preexposure plus heat (5.68±0.4%) all showed significant changes in ATP compared to untreated control (1.30E-05<P<4.36E-05). On the contrary, cells exposed to heat alone showed little signs of intracellular ATP depletion (86.1±10.1%, n=12, FIG. 12B).

Mitochondrial Enzyme Activity Immediately after Treatment

Long-term P85 exposure induced a greater than 2 fold increase in viability (249.0±10.4%) compared to untreated control (P=5.25E-05), and acute P85 exposure under heat led to an increase of 130.0±16.4%. Combination of P85 preexposure with heat caused a significant decrease in viability (48.6±7.2%) compared to untreated control (P=1.61E-02) and all other treatment conditions (1.99E-10<P<1.33E-02). Again, in comparison, heat alone caused a relatively minor change (85.3±6.2%) (FIG. 12B, n=12).

Change in Intracellular ATP Twenty Four Hours after Treatment

ATP, which was significantly depleted immediately after treatment, recovered to 87.4±9.5% of control in cells which received long-term P85 alone and to 118.0±11.5% for cells receving acute P85 under heat. Conversely, when cells were exposed to heat alone, the intracellular ATP level was 90.7±9.7%, and did not change relative to that detected immediately after treatment. Most importantly, very little recovery (27.3±2.8%) of intracellular ATP was detected when cells received the combination of P85 preexposure with heat (FIG. 12B, n=12). Significant differences were observed between combination of P85 preexposure with heat and untreated control (P=6.07E-08), and between combination of P85 preexposure with heat and all other treatment groups (4.73E-06<P<2.93E-4).

Mitochondrial Enzyme Activity Twenty Four Hours after Treatment

Results from this assay illustrated that both heat alone (48.4±5.8%, P=1.00E-04) and combination of P85 pre-exposure with heat (17.4±3.6%, P=3.93E-07) led to a significant decrease in cell viability. The most pronounced decrease was observed in cells which received combination of P85 pre-exposure with heat. Similarly to that detected immediately after the treatment, the viability of cells receiving long-term P85 was still significantly higher than that of untreated control (137.0±8.2%, P=5.77E-03, FIG. 12B, n=12). Significant differences were also seen between combination of P85 pre-exposure and all other treatment conditions (8.94E-10<P<1.61E-03). Again, significantly increased viability was detected in cells receiving acute P85 under heat compared to cells had heat alone treatment (P=2.46E-05).

Discussion and Conclusions

In this study we investigated the thermal sensitizing effects of Pluronic P85 and its mechanism of thermal sensitization on two different cell lines, a rat colorectal adenocarcinoma, DHD/K12/TRb and a human glioma, luciferase transfected Glio36Δ5. Results showed that in both cell lines low-grade hyperthermia alone caused little or no change in cell viability and had only minor influence on intracellular ATP production. While P85 alone led to a decrease in viability and significant ATP depletion immediately after treatment, a full recovery of cell viability was seen 24 after removal of the sensitizer. However, when 240 min P85 pre-exposure was followed by 15 min of hyperthermia at 43° C. a significant decrease in viability and ATP was seen in both cell lines even after the 24 hour recovery period. More significant decreases were observed in the luciferase transfected Glio36Δ5 cells, suggestions that P85 caused severe intracellular ATP depletion in Gio36Δ5 cells. The diminished proliferation ability was confirmed with clonogenic survival studies showing that P85, when combined with heat shock, significantly inhibited colony formation. These results indicate that an appropriate dose and pre-exposure duration of Pluronic P85 in synergy with low-grade, sublethal heat may be a more effective approach than hyperthermic cancer treatment alone.

Results of this study have shown that P85 was able to significantly deplete intracellular ATP, particularly in Glio36Δ5 cells. This finding is consistent with a previous study by Batrakova et. al. (Batrakova, E. V. et al., *Pharm Res* 20:1581-1590, 2003). While ATP depletion can be either due to excessive cellular consumption or a destabilization in its production machinery, the later is inconsistent with our findings, since normal cellular metabolism was resumed upon removal of P85. This function should be seen in all cells, yet it was not observed in our results, where the DHD/K12/TRb cells showed significantly increased ATP levels under the aforementioned conditions. From here, we can speculate that the intracellular P85 did not impair the ATP production machinery, but instead exhausted its intracellular supply.

From these results we can also conclude that P85 may sensitize cells to hyperthermic injury through more than one pathway in concert. ATP was increased up to 80% in one cell line (DHD/K12/TRb) and depleted almost completely in another (Glio36Δ5) immediately after treatment, while the final outcome collectively showed significantly decreased viability and proliferation ability. It is thus possible that P85 interacts with a specific ATP-dependent membrane protein leading to leakage of cellular ionic species hence an overworked pump, i.e., G-glycoprotein, causing ATP exhaustion in the Glio36Δ5 cell line. Alternatively, P85 may have affected the apoptosis pathway (Minko, T. et al., *J Control Release* 105:269-278, 2005) in DHD/K12/TRb cells causing cellular stress that further signals increased output (increase in ATP production) for self protection, i.e., producing heat shock protein (hsp) (Trieb, K. et al., *Cell Biochem Funct* 25:669-672, 2007). Heat shock response is characterized by i) induction of heat shock protein synthesis, and ii) inhibition of many metabolic pathways in prevention of uncontrollable and unpredictable production of toxic proteins (Lebret, T. et al., *J Urol* 169:338-346, 2003; Roigas, J. et al., *Prostate* 34:195-202, 1998; Sreedhar, A. S. et al., *FEBS Lett* 456:339-342, 1999). Upon removal of stress, the heat shock response diminishes (Lindquist, S., *Annu Rev Biochem* 55:1151-1191, 1986; Solomon, J. M. et al., *New Biol* 3:1106-1120, 1991).

This may explain why cells receiving acute P85 under heat had increased viability in both cell lines (FIG. 12A). The same explanation can be used to elucidate why cells receiving 30 or 45 min of heat had higher intracellular ATP levels compared to cells receiving 15 min of heat in addition to 240 min of P85 preexposure at 10 mg/mL (FIG. 9B).

Previous studies have shown that Pluronic induces ATP depletion selectively in multi drug resistant (MDR) cell but not in non-MDR cells (Batrakova, E. V. et al., *Br J Cancer* 85:1987-1997, 2001). P85 was able to deplete intracellular ATP in luciferase transfected Glio36Δ5 cells but not in the non-multidrug resistant DHD/K12/TRb cells, suggesting that the Glio36Δ5 cell line may express the MDR phenotype. Since many difficult to manage cancers are MDR resistant (Lage, H. et al., *Lancet Oncol* 1:169-175, 2000; Kuttesch, J. F. et al., *Invest New Drugs* 14:55-67, 1996) and overexpress ATP dependent membrane proteins (Gottesman, M. M. et al., *Curr Opin Genet Dev* 6:610-617, 1996) relative to the parenchyma, P85 may be used selectively to sensitize these cells and preserve normal surrounding tissue.

In this study, we have demonstrated that Pluronic P85 is able to inhibit the recovery of normal cellular metabolism after low-grade hyperthermic shock in a dose and time dependent manner. The observed effects vary by cell type, presumably due to multiple pathways affected by the sensitizer. Pluronic is currently undergoing phase III clinical trials as a chemo-sensitizer for treatment of MDR cancers (Kabanov, A. V. et al., *Adv Drug Deliv Rev* 54:759-779, 2002; Kabanov, A. V. et al., *J Control Release* 91:75-83, 2003). With a proven safety profile and proof of concept presented in the current study, this sensitizer in concert with hyperthermia could lead to a safe, efficacious and potentially selective cancer treatment.

From the above description of the invention, those skilled in the art will perceive improvements, changes and modifications. Such improvements, changes and modifications are within the skill of those in the art and are intended to be covered by the appended claims.

Having described the invention, we claim:

1. A method for treating a cancer or tumor in a subject, the method consisting essentially of:
    administering to cancer or tumor cells of the cancer or tumor a thermosensitizing amount of a neoplastic cell-sensitizing composition comprising a poly(ethylene oxide)-poly(propylene oxide) copolymer having the chemical formula of:

$HO-(C_2H_4O)_a(C_3H_6O)_b(C_2H_4O)_a-H$, where "a" is about 2 to about 130 and "b" is about 16 to about 70, the copolymer sensitizing the cancer or tumor cells to hyperthermia; and
    applying energy to the sensitized cancer or tumor cells to heat and ablate the sensitized cancer or tumor cells.

2. The method of claim 1, the copolymer having the chemical formula of:

$HO-(C_2H_4O)_{26}(C_3H_6O)_{40}(C_2H_4O)_{26}-H$.

3. The method of claim 1, the neoplastic cell-sensitizing composition being injected directly into the tumor.

4. The method of claim 1, the neoplastic cell-sensitizing composition being administered parenterally.

5. The method of claim 1, the neoplastic cell-sensitizing composition being administered by intravenous injection.

6. The method of claim 1, the energy comprising at least one of ultrasonic energy or electromagnetic energy.

7. The method of claim 6, the electromagnetic energy comprising at least one of radiofrequency (RF) energy, x-ray energy, infrared radiation, far infrared radiation, ultraviolet radiation, long-wavelength ultraviolet radiation, a visible light, microwave energy or γ-ray radiation.

8. The method of claim 7, the electromagnetic energy comprising RF energy and the RF energy being applied to the sensitized tumor or cancer cells to heat and ablate the sensitized tumor or cancer cells.

9. A method for treating a tumor in a subject, the method consisting essentially of:
    administering to neoplastic cells of the tumor a thermosensitizing amount of a neoplastic cell-sensitizing composition comprising a poloxamer having the chemical formula of:

$HO-(C_2H_4O)_a(C_3H_6O)_b(C_2H_4O)_a-H$, where "a" is about 2 to about 130 and "b" is about 16 to about 70, the poloxamer sensitizing the tumor to hyperthermia; and
    applying energy to the sensitized neoplastic cells of the tumor to heat and ablate the sensitized neoplastic cells.

10. The method of claim 9, the poloxamer having the chemical formula of:

$HO-(C_2H_4O)_{26}(C_3H_6O)_{40}(C_2H_4O)_{26}-H$.

11. The method of claim 9, the neoplastic cell-sensitizing composition being injected directly into the tumor.

12. The method of claim 9, the neoplastic cell-sensitizing composition being administered intravenously.

13. The method of claim 9, the energy comprising at least one of electromagnetic energy or ultrasonic energy.

14. The method of claim 9, the energy comprising RF energy and the RF energy being applied to the sensitized tumor cells to heat and ablate the sensitized tumor cells.

15. A method for treating a tumor in a subject, the method consisting essentially of:
    administering to neoplastic cells of the tumor a thermosensitizing amount of neoplastic cell-sensitizing composition comprising a poloxamer having the chemical formula of:

$HO-(C_2H_4O)_a(C_3H_6O)_b(C_2H_4O)_a-H$, where "a" is about 2 to about 130 and "b" is about 16 to about 70, the poloxamer sensitizing the neoplastic cells to radiofrequency ablation; and
    ablating the sensitized neoplastic cells of the tumor with radiofrequency energy.

16. The method of claim 15, the poloxamer having the chemical formula of:

$HO-(C_2H_4O)_{26}(C_3H_6O)_{40}(C_2H_4O)_{26}-H$.

17. The method of claim 15, the neoplastic cell-sensitizing composition being administered directly to the neoplastic cells.

18. The method of claim 15, the neoplastic cell-sensitizing composition being administered intravenously.

* * * * *